(12) United States Patent
Pai et al.

(10) Patent No.: US 11,634,383 B2
(45) Date of Patent: Apr. 25, 2023

(54) METHOD OF PREPARING DIISOCYANATE COMPOSITION

(71) Applicants: SKC CO., LTD., Gyeonggi-do (KR); WOORI FINE CHEM CO., LTD., Gyeonggi-do (KR)

(72) Inventors: Jaeyoung Pai, Gyeonggi-do (KR); Jeongmoo Kim, Gyeonggi-do (KR); Jung Hwan Myung, Gyeonggi-do (KR); Hyuk Hee Han, Gyeonggi-do (KR)

(73) Assignees: SKC CO., LTD., Gyeonggi-do (KR); WOORI FINE CHEM CO., LTD, Gyeonggi-do (KR)

( * ) Notice: Subject to any disclaimer, the term of this patent is extended or adjusted under 35 U.S.C. 154(b) by 0 days.

(21) Appl. No.: 17/111,726

(22) Filed: Dec. 4, 2020

(65) Prior Publication Data
US 2021/0171446 A1    Jun. 10, 2021

(30) Foreign Application Priority Data

Dec. 6, 2019  (KR) .................. 10-2019-0161539
Dec. 6, 2019  (KR) .................. 10-2019-0161696
Dec. 6, 2019  (KR) .................. 10-2019-0161697

(51) Int. Cl.
*C07C 263/20*    (2006.01)
*C07C 265/14*    (2006.01)

(52) U.S. Cl.
CPC .......... *C07C 263/20* (2013.01); *C07C 265/14* (2013.01)

(58) Field of Classification Search
CPC .............. C07C 263/10; C07C 263/20; C07C 265/14; C07C 265/08; B29D 11/00009; C08G 18/3855; C08G 18/3874; C08G 18/7642; G02B 1/041; Y02P 20/582
See application file for complete search history.

(56) References Cited

U.S. PATENT DOCUMENTS

| | | | | |
|---|---|---|---|---|
| 3,410,888 A | * | 11/1968 | Hammond | C07C 265/14 560/347 |
| 3,492,331 A | * | 1/1970 | Ulrich | C07C 265/14 560/347 |
| 2021/0230352 A1 | * | 7/2021 | Kim | C07C 209/00 |

FOREIGN PATENT DOCUMENTS

| | | | |
|---|---|---|---|
| CN | 1931824 A | | 3/2007 |
| CN | 106674056 | * | 5/2017 |
| CN | 106748887 | * | 5/2017 |
| KR | 1994-0001948 B1 | | 3/1994 |

OTHER PUBLICATIONS

CN106748887 translated (Year: 2017).*
Eckert et al. (Triphosgene, a Crystalline Phosgene Substitute, Angew. Chem. Int. Ed. Engl. 26, No. 9, pp. 894-895, Published 1987) (Year: 1987).*
Armarego et al. (Purification of Laboratory Chemicals 6th Edition, total pages 4, Published 2009) (Year: 2009).*
THF or Et2O (Year: 2019).*
CN106674056 translated (Year: 2017).*
Office Action for application 202011431035.2 issued by the Chinese Patent Office dated May 18, 2022.

* cited by examiner

*Primary Examiner* — Yevgeny Valenrod
*Assistant Examiner* — Blaine G Doletski
(74) *Attorney, Agent, or Firm* — IP & T Group LLP

(57) ABSTRACT

The embodiments provide processes for preparing a diisocyanate composition and an optical lens, which are excellent in yield and quality with mitigated environmental problems by using a solid triphosgene composition instead of phosgene gas in the process of preparing a diisocyanate from a diamine through a hydrochloride thereof and by controlling the content of a decomposition product in a triphosgene composition, the b* value according to CIE color coordinate of the triphosgene composition in an organic solvent, or the content of water in the triphosgene.

6 Claims, 1 Drawing Sheet

[Fig. 1A]
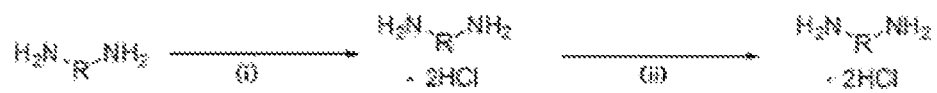
[Fig. 1B]
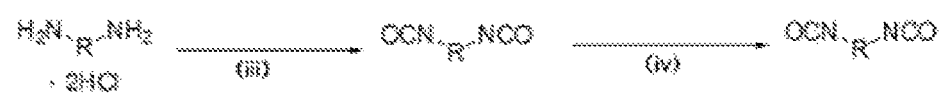
[Fig. 2]
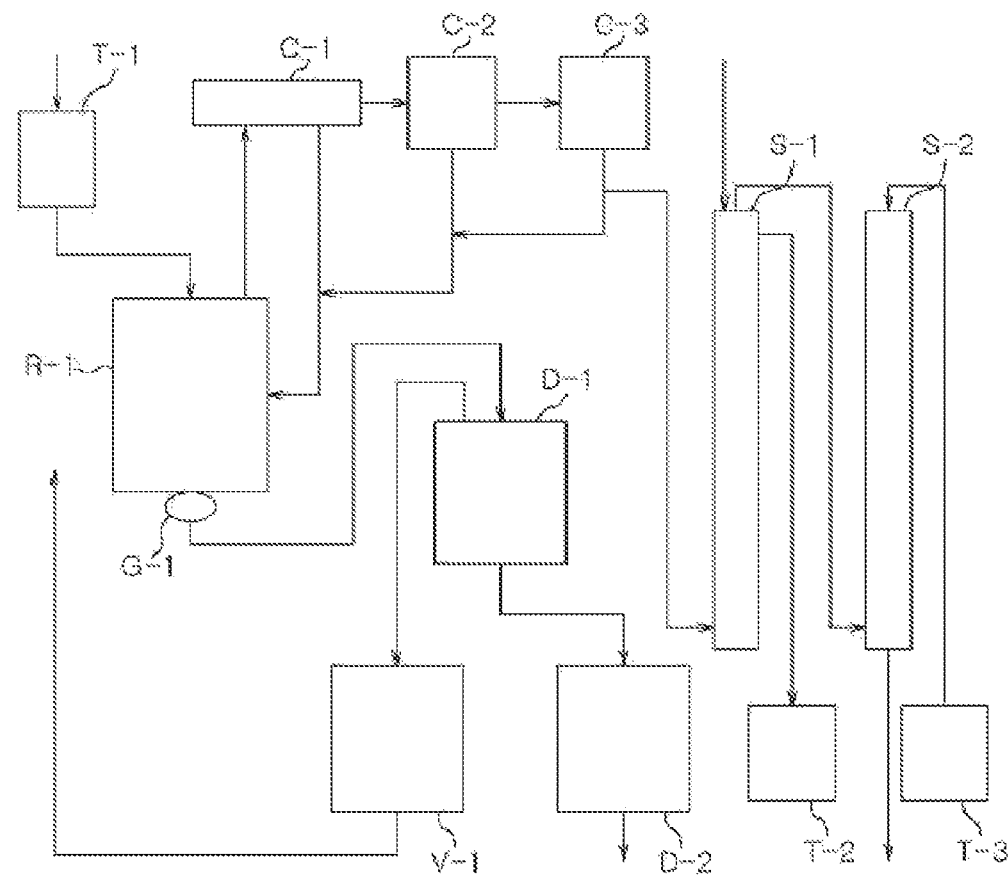

METHOD OF PREPARING DIISOCYANATE COMPOSITION

The present application claims priority of Korean patent application numbers 110-2019-0161539 filed on Dec. 6, 2019, 10-2019-0161696 filed on Dec. 6, 2019 and 10-2019-0161697 filed on Dec. 6, 2019, The disclosure of each of the foregoing applications is incorporated herein by reference in its entirety.

TECHNICAL FIELD

Embodiments relate to a process for preparing a diisocyanate composition. More specifically, the embodiments relate to a process for preparing a diisocyanate composition through a diamine hydrochloride, a process for preparing an optical lens using the diisocyanate composition thus prepared, and a triphosgene composition having a specific content of components and used in the above preparation.

BACKGROUND ART

Isocyanates used as a raw material for plastic optical lenses are prepared by a phosgene method, a non-phosgene method, a pyrolysis method, or the like.

In the phosgene method, an amine as a raw material is reacted with phosgene ($COCl_2$) gas to synthesize an isocyanate. In addition, in the non-phosgene method, xylylene chloride is reacted with sodium cyanate in the presence of a catalyst to synthesize an isocyanate. In the pyrolysis method, an amine is reacted with an alkyl chloroformate to prepare a carbamate, which is pyrolyzed in the presence of a catalyst at a high temperature to synthesize an isocyanate.

The phosgene method among the above methods for preparing isocyanates is the most widely used. In particular, a direct method in which an amine is directly reacted with phosgene gas has been commonly used. But it has a problem that a plurality of apparatuses for the direct reaction of phosgene gas are required. Meanwhile, in order to supplement the direct method, a hydrochloride method has been developed in which an amine is reacted with hydrogen chloride gas to obtain an amine hydrochloride as an intermediate, which is reacted with phosgene, as disclosed in Korean Patent Publication No. 1994-1948.

In the method of obtaining hydrochloride as an intermediate by reacting an amine with hydrogen chloride gas among the conventional phosgene methods for synthesizing isocyanates, a hydrochloride is produced as fine particles at atmospheric pressure, so that the agitation inside the reactor is not smoothly carried out. Thus, an additional process of raising the temperature to increase the pressure inside the reactor is required, and there is a problem that the yield of the final product is low as well.

Thus, an attempt has been made to obtain a hydrochloride using an aqueous hydrochloric acid solution instead of hydrogen chloride gas. However, as the amine is dissolved in the aqueous hydrochloric acid solution, the yield is significantly reduced to 50%, making it difficult to be applied in practice. There is a difficulty in that an amine having a low content of water and impurities should be used as a raw material in order to increase the purity of the final product. In addition, phosgene gas used in the conventional phosgene method is highly toxic and is a substance subject to environmental regulations. There is a difficulty in storage and management since a separate cooling apparatus is required to store it.

DETAILED DESCRIPTION OF THE INVENTION

Technical Problem

Accordingly, the present inventors have been able to solve the conventional environmental, yield, and quality problems in the process of preparing a diisocyanate, which is mainly used as a raw material for plastic optical lenses, from a diamine through a hydrochloride thereof by way of using an aqueous hydrochloric acid solution instead of hydrogen chloride gas and solid triphosgene instead of phosgene gas while adjusting the reaction conditions.

In addition, the present inventors have focused that triphosgene is in part decomposed by various causes such as air, metal salt, silica gel, dust, heat, and the like to generate decomposition products such as phosgene, carbon dioxide, and carbon tetrachloride; as a result, it exists in the form of a composition mixed with these decomposition products. In particular, the present inventors have discovered that if a triphosgene composition containing decomposition products in a certain amount or more is used to prepare a diisocyanate composition, the color and haze may be deteriorated, and it may have an impact on the stria, transmittance, yellow index, and refractive index of the final optical lens.

In addition, the present inventors have focused that triphosgene reacts with moisture in the air during storage to generate phosgene, which in turn reacts with moisture in the air to increase the b* value according to the CIE color coordinate. In particular, the present inventors have discovered that if a triphosgene composition having a b* value of a certain level or more is used to prepare a diisocyanate composition, the color and haze may be deteriorated, and it may have an impact on the stria, transmittance, yellow index, and refractive index of the final optical lens. In addition, if distillation is carried out several times in order to make a discolored diisocyanate composition colorless and transparent, it may cause a loss in yield, thereby decreasing the economic efficiency.

In addition, the present inventors have focused that when water is contained in triphosgene used in the phosgenation reaction for the preparation of a diisocyanate, side reactions take place, thereby reducing the number of equivalents for the reaction, and it also reacts with a diisocyanate to form urea, which significantly reduces the yield and purity of the final product. In particular, the present inventors have discovered that it is possible to effectively control the content of water if triphosgene is washed with a solvent having a certain range of polarity index and boiling point without a nucleophilic group.

Accordingly, an object of the embodiments is to provide processes for preparing a diisocyanate composition and an optical lens capable of enhancing the optical characteristics by controlling the content of a decomposition product in a triphosgene composition, the b* value according to CIE color coordinate of the triphosgene composition in an organic solvent, or the content of water in the triphosgene.

Solution to the Problem

According to an embodiment, there is provided a process for preparing a diisocyanate composition, which comprises reacting a diamine hydrochloride composition with a triphosgene composition to obtain a diisocyanate composition, wherein the content of a decomposition product of triphosgene in the triphosgene composition is less than 1% by weight.

According to another embodiment, there is provided a process for preparing a diisocyanate composition, which comprises reacting a diamine hydrochloride composition with a triphosgene composition to obtain a diisocyanate composition, wherein the triphosgene composition has a b* value according to the CIE color coordinate of 1.2 or less when dissolved in orthodichlorobenzene at a concentration of 8% by weight.

According to still another embodiment, there is provided a process for preparing a diisocyanate composition, which comprises reacting a diamine with an aqueous hydrochloric acid solution to obtain a diamine hydrochloride composition; and reacting the diamine hydrochloride composition with triphosgene to obtain a diisocyanate composition, wherein the content of water in the triphosgene is 200 ppm or less.

Advantageous Effects of the Invention

In the process for preparing a diisocyanate according to the above embodiment, phosgene gas, which is highly toxic and has difficulties in storage and management, is not used. Instead, triphosgene, which is less toxic and does not require a separate cooling storage apparatus since it is solid at room temperature, is used; thus, it is excellent in the handling convenience and processability. In particular, according to the above embodiment, it is possible to enhance the color and haze of a diisocyanate composition and to enhance the stria, transmittance, yellow index, and refractive index of the final optical lens by controlling the content of a decomposition product in a triphosgene composition, the b* value according to CIE color coordinate of the triphosgene composition in an organic solvent, or the content of water in the triphosgene.

In addition, in the process for preparing a diisocyanate according to the more preferable embodiment, an aqueous hydrochloric acid solution, without the use of hydrogen chloride gas, is used to prepare a diamine hydrochloride as an intermediate. Since the reaction can be carried out even at atmospheric pressure, an additional apparatus for high-temperature heating and cooling is not required, and the yield can be further enhanced.

Accordingly, the process for preparing a diisocyanate composition according to the embodiment can be applied to the preparation of a plastic optical lens of high quality.

BRIEF DESCRIPTION OF THE DRAWINGS

FIG. 1A and FIG. 1B schematically show the process for preparing a diisocyanate composition according to an embodiment.

FIG. 2 shows an example of the process equipment for the reaction of a diamine hydrochloride and triphosgene.

REFERENCE NUMERALS OF THE DRAWINGS

T-1: first tank, T-2: second tank, T-3: third tank
R-1: reactor, D-1: first distiller, D-2: second distiller
C-1: first condenser, C-2: second condenser, C-3: third condenser
S-1: first scrubber, S-2: second scrubber
G-1: viewing window, V-1: solvent recovery apparatus.

BEST MODE FOR CARRYING OUT THE INVENTION

Throughout the present specification, when a part is referred to as "comprising" an element, it is understood that other elements may be comprised, rather than other elements are excluded, unless specifically stated otherwise.

In addition, all numbers and expression related to the physical properties, contents, dimensions, and the like used herein are to be understood as being modified by the term "about," unless otherwise indicated.

In the present specification, an "amine" refers to a compound having one or more amine groups at the terminal, and a "diamine" refers to a compound having two amine groups at the terminal. They may have a wide variety of structures depending on the skeleton of an aliphatic chain, an aliphatic ring, and an aromatic ring. Specific examples of the diamine include xylylenediamine (XDA), hexamethylenediamine (HDA), 2,2-dimethylpentanediamine, 2,2,4-trimethylhexanediamine, butenediamine, 1,3-butadiene-1,4-diamine, 2,4,4-trimethylhexamethylenediamine, bis(aminoethyl)carbonate, 4,4'-methylenediamine (MDA), bis(aminoethyl) ether, bis(aminoethyl)benzene, bis(aminopropyl)benzene, α,α,α',α'-tetramethylxylylenediamine, bis(aminobutyl)benzene, bis(aminomethyl)naphthalene, bis(aminomethyl)diphenyl ether, bis(aminoethyl)phthalate, 2,6-di(aminomethyl)furan, hydrogenated xylylenediamine (H6XDA), dicyclohexylmethanediamine, cyclohexanediamine, methylcyclohexanediamine, isophoronediamine (IPDA), dicyclohexyldimethylmethanediamine, 2,2-dimethyldicyclohexylmethanediamine, 2,5-bis(aminomethyl)bicyclo-[2,2,1]-heptane, 2,6-bis(aminomethyl)bicyclo-[2,2,1]-heptane, 3,8-bis(aminomethyl)tricyclodecane, 3,9-bis(aminomethyl)tricyclodecane, 4,8-bis(aminomethyl)tricyclodecane, 4,9-bis(aminomethyl)tricyclodecane, norbornenediamine (NBDA), bis(aminomethyl) sulfide, bis(aminoethyl) sulfide, bis(aminopropyl) sulfide, bis(aminohexyl) sulfide, bis(aminomethyl) sulfone, bis(aminomethyl) disulfide, bis(aminoethyl) disulfide, bis(aminopropyl) disulfide, bis(aminomethylthio) methane, bis(aminoethylthio)methane, bis(aminoethylthio) ethane, and bis(aminomethylthio)ethane. More specifically, the diamine may be at least one selected from the group consisting of xylylenediamine (XDA), norbornenediamine (NBDA), hydrogenated xylylenediamine (H6XDA), isophoronediamine (IPDA), and hexamethylenediamine (HDA). The xylylenediamine (XDA) includes orthoxylylenediamine (o-XDA), metaxylylenediamine (m-XDA), and paraxylylenediamine (p-XDA).

In the present specification, an "isocyanate" refers to a compound having an NCO group, a "diisocyanate" refers to a compound having two NCO groups at the terminal. They may have a wide variety of structures depending on the skeleton of an aliphatic chain, an aliphatic ring, and an aromatic ring. Specific examples of the diamine include xylylene diisocyanate (XDI), hexamethylene diisocyanate (HDI), 2,5-bis(isocyanatomethyl)-bicyclo[2.2.1]heptane, 2,6-bis(isocyanatomethyl)-bicyclo[2.2.1]heptane, hydrogenated xylylene diisocyanate (H6XDI), dicyclohexylmethane diisocyanate, isophorone diisocyanate (IPDI), 1,2-diisocyanatobenzene, 1,3-diisocyanatobenzene, 1,4-diisocyanatobenzene, 2,4-diisocyanatotoluene, ethylphenylene diisocyanate, dimethylphenylene diisocyanate, biphenyl diisocyanate, toluidine diisocyanate, 4,4'-methylenebis(phenylisocyanate) (MDI), 1,2-bis(isocyanatomethyl)benzene, 1,3-bis(isocyanatomethyl)benzene, 1,4-bis(isocyanatomethyl)benzene, 1,2-bis(isocyanatoethyl)benzene, 1,3-bis(isocyanatoethyl)benzene, 1,4-bis(isocyanatoethyl)benzene, α,α,α',α'-tetramethylxylylene diisocyanate, bis(isocyanatomethyl)naphthalene, bis(isocyanatomethylphenyl) ether, norbornene diisocyanate (NBDI), bis(isocyanatomethyl) sulfide, bis(isocyanatoethyl) sulfide, bis(isocyanatopropyl) sulfide, 2,5-diisocyanatotetrahydrothiophene, 2,5- diisocyanatomethyltetrahydrothiophene, 3,4-diisocyanatomethyltetrahydrothiophene, 2,5-diisocyanato-1,4-dithiane, and 2,5-diisocyanatomethyl-1,4-dithiane. More specifically, the diisocyanate may be at least one selected from the group consisting of xylylene diisocyanate (XDI), norbornene diisocyanate (NBDI), hydrogenated xylylene diisocyanate (H6XDI), isophorone diisocyanate (IPDI), and hexamethylene diisocyanate (HDI). The xylylene diisocyanate (XDI) includes orthoxylylene diisocyanate (o-XDI), metaxylylene diisocyanate (m-XDI), and paraxylylene diisocyanate (p-XDIA).

In the present specification, as is well known, a "composition" may refer to a form in which two or more chemical components are mixed or combined in a solid, liquid, and/or gas phase while generally maintaining their respective unique properties.

The compounds used in each reaction step according to the above embodiment (e.g., triphosgene) or the compounds obtained as a result of the reaction (e.g., diamine hydrochloride, diisocyanate) are generally present in a mixed or combined state with heterogeneous components generated as unreacted raw materials in each reaction step, as side reactions or reaction with water, or as natural decomposition of the compounds. A trace amount of these components may remain to exist with the main components.

According to the embodiment, since attention is paid to these heterogeneous components mixed or combined with the main compounds, even a trace amount of the heterogeneous components is treated as a composition mixed or combined with the main compounds to specifically illustrate the components and contents thereof.

In addition, in the present specification, for clear and easy distinction between various compositions, terms are also described in combination with the names of the main components in the composition. For example, a "diamine hydrochloride composition" refers to a composition comprising a diamine hydrochloride as a main component, a "triphosgene composition" refers to a composition comprising triphosgene as a main component, and a "diisocyanate composition" refers to a composition comprising a diisocyanate as a main component. In such event, the content of the main component in the composition may be 50% by weight or more, 80% by weight or more, or 90% by weight or more, for example, 90% by weight to 99.9% by weight.

In this specification, the unit of ppm refers to ppm by weight.

[Process for Preparing a Diisocyanate Composition]

The process for preparing a diisocyanate composition according to an embodiment comprises reacting a diamine hydrochloride composition with a triphosgene composition to obtain a diisocyanate composition, wherein the content of a decomposition product of triphosgene in the triphosgene composition is less than 1% by weight.

The process for preparing a diisocyanate composition according to another embodiment comprises reacting a diamine hydrochloride composition with a triphosgene composition to obtain a diisocyanate composition, wherein the triphosgene composition has a b* value according to the CIE color coordinate of 1.2 or less when dissolved in orthodichlorobenzene at a concentration of 8% by weight.

The diamine hydrochloride composition may be obtained by reacting a diamine with an aqueous hydrochloric acid solution. Specifically, the process for preparing a diisocyanate composition according to the embodiment further comprises reacting a diamine with an aqueous hydrochloric acid solution to obtain a diamine hydrochloride composition.

The process for preparing a diisocyanate composition according to still another embodiment comprises reacting a diamine with an aqueous hydrochloric acid solution to obtain a diamine hydrochloride composition; and reacting the diamine hydrochloride composition with triphosgene to obtain a diisocyanate composition, wherein the content of water in the triphosgene is 200 ppm or less.

FIG. 1A and FIG. 1B schematically show the process for preparing a diisocyanate composition according to an embodiment. In FIG. 1A and FIG. 1B, R comprises an aromatic ring, an aliphatic ring, an aliphatic chain, and the like. As a specific example, R may be xylylene, norbornene, hydrogenated xylylene, isophorone, or hexamethylene, but it is not limited thereto.

In FIG. 1A, (i) may comprise a step of adding an aqueous hydrochloric acid solution to react a diamine with the aqueous hydrochloric acid solution. In FIG. 1A, (ii) may comprise at least one step selected from a precipitation step, a filtration step, a drying step, and a washing step. In FIG. 1B, (iii) may comprise a step of adding triphosgene to react a diamine hydrochloride composition with triphosgene. In FIG. 1B, (iv) may comprise at least one step selected from a degassing step, a filtration step, and a distillation step.

Hereinafter, each step will be described in detail.

Preparation of a Diamine Hydrochloride Composition

First, a diamine is reacted with an aqueous hydrochloric acid solution to obtain a diamine hydrochloride composition.

In addition, after the reaction of the diamine composition and the aqueous hydrochloric acid solution, a first organic solvent may be further introduced to obtain the diamine hydrochloride composition in a solid phase.

The following Reaction Scheme 1 shows an example of the reaction in this step.

[Reaction Scheme 1]

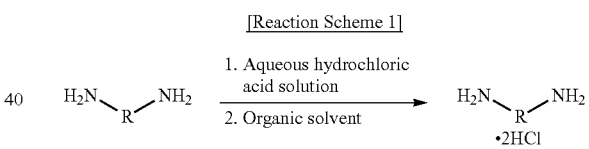

In the above scheme, R comprises an aromatic ring, an aliphatic ring, an aliphatic chain, and the like. As a specific example, R may be xylylene, norbornene, hydrogenated xylylene, isophorone, or hexamethylene, but it is not limited thereto.

In the conventional method in which hydrogen chloride gas is used, a hydrochloride is produced as fine particles upon the reaction at atmospheric pressure, so that the agitation inside the reactor is not smoothly carried out. Thus, an additional process of raising the pressure to increase the internal temperature of the reactor is required, and there is a problem that the yield of the final product is low as well.

According to the above embodiment, however, since an aqueous hydrochloric acid solution is used, it is possible to solve the problem involved in the prior art in which hydrogen chloride gas is used. Specifically, when an aqueous hydrochloric acid solution is used, the product obtained through the reaction is in a solid form rather than a slurry form, so that the yield is high. The reaction can be carried out even at atmospheric pressure, so that a separate apparatus or process for rapid cooling is not required.

The concentration of the aqueous hydrochloric acid solution may be 5% by weight to 50% by weight. Within the above concentration range, it is possible to minimize the dissolution of the hydrochloride in the aqueous hydrochloric acid solution, thereby enhancing the final yield, and to improve the handling convenience.

Specifically, the concentration of the aqueous hydrochloric acid solution may be 10% by weight to 45% by weight, 20% by weight to 45% by weight, or 30% by weight to 40% by weight. More specifically, the aqueous hydrochloric acid solution may have a concentration of 20% by weight to 45% by weight.

The diamine and the aqueous hydrochloric acid solution may be introduced to the reaction at an equivalent ratio of 1:2 to 5. If the equivalent ratio is within the above range, it is possible to reduce the unreacted materials and to prevent a decrease in the yield caused by dissolution as water is generated. Specifically, the diamine and the aqueous hydrochloric acid solution may be introduced to the reaction at an equivalent ratio of 1:2 to 2.5.

The introduction of the diamine and the aqueous hydrochloric acid solution may be carried out while the internal temperature of the reactor is maintained to be constant. When the diamine and the hydrochloric acid aqueous solution are introduced, the internal temperature of the reactor may be in the range of 20° C. to 100° C. Within the above temperature range, it is possible to prevent the temperature from being raised above the boiling point, which is not suitable for the reaction, or the temperature from being lowered too much, whereby the reaction efficiency is reduced.

Specifically, when the diamine and the hydrochloric acid aqueous solution are introduced, the internal temperature of the reactor may be 20° C. to 60° C. or 20° C. to 40° C. More specifically, the diamine and the aqueous hydrochloric acid solution may be introduced to the reaction at an equivalent ratio of 1:2 to 5 at a temperature of 20° C. to 40° C.

In the conventional hydrochloride method, a large amount of heat is generated in the reaction, which requires rapid cooling through a separate cooler, whereas the reaction materials are introduced while a low temperature is maintained according to the above embodiment, which does not require a separate cooler.

The introduction of the diamine and the aqueous hydrochloric acid solution may be carried out, for example, in a sequence in which the hydrochloric acid aqueous solution may be first introduced to the reactor and the diamine may then be slowly introduced to the reactor. The introduction of the diamine and/or the aqueous hydrochloric acid solution may be carried out for 30 minutes to 1 hour.

When the introduction of the diamine and the hydrochloric acid aqueous solution is completed, the internal temperature of the reactor may be lowered to 0° C. to 20° C., 0° C. to 10° C., or 10° C. to 20° C.

The reaction between the diamine and the aqueous hydrochloric acid solution may be carried out at atmospheric pressure for, for example, 30 minutes to 2 hours with stirring.

As a result of the reaction between the diamine and the aqueous hydrochloric acid solution, a diamine hydrochloride composition in an aqueous solution form may be obtained as the reaction resultant.

Thereafter, a step of treating the diamine hydrochloride composition may be further carried out. For example, the step of treating the diamine hydrochloride composition may comprise at least one of precipitating the diamine hydrochloride composition, filtering the diamine hydrochloride composition, drying the diamine hydrochloride composition, and washing the diamine hydrochloride composition.

Specifically, a first organic solvent may be introduced to the reaction resultant to precipitate a solid diamine hydrochloride composition. That is, the first organic solvent may induce the precipitation of a solid diamine hydrochloride composition through crystallization. More specifically, the first organic solvent may be introduced to the reaction resultant, which is cooled and further stirred to carry out the reaction.

Specifically, the first organic solvent may be at least one selected from the group consisting of diethyl ether, diisopropyl ether, dioxane, tetrahydrofuran, methanol, ethanol, dimethyl sulfoxide, dimethylformamide, acetonitrile, acetone, trichloroethylene, tetrachloroethane, trichloroethanol, n-butanol, isobutanol, methyl ethyl ketone, methyl butyl ketone, isopropanol, hexane, chloroform, and methyl acetate.

The amount (weight) of the first organic solvent introduced may be 1 to 5 times the weight of the diamine. If the introduced amount is within the above range, it is possible to prevent the use of excessive organic solvents while the yield of the final hydrochloride is high. Specifically, the first organic solvent may be introduced to the reaction in an amount of 1 to 2 times, 1 to 1.5 times, or 1.3 to 1.5 times, the weight of the diamine.

After the first organic solvent is introduced, the cooling temperature may be −10° C. to 10° C. or −5° C. to 5° C. In addition, the additional reaction time after cooling may be 30 minutes to 2 hours or 30 minutes to 1 hour.

According to a specific example, the steps of (1a) introducing the aqueous hydrochloric acid solution to a first reactor; (1b) introducing the diamine to the first reactor and stirring them; and (1c) introducing the first organic solvent to the first reactor and stirring them may be sequentially carried out.

More specifically, the process may further comprise cooling the inside of the reactor to a temperature of 0° C. to 10° C. after the introduction of the diamine and before stirring in step (1 b); and cooling the inside of the reactor to a temperature of −5° C. to 5° C. after the introduction of the first organic solvent and before stirring in step (1c).

After the first organic solvent is introduced, separation, filtration, washing, and drying may be further carried out. For example, after the first organic solvent is introduced, the aqueous layer may be separated, filtered, washed, and dried to obtain a solid diamine hydrochloride composition. The washing may be carried out one or more times using, for example, a solvent having a polarity index of 5.7 or less. In addition, the drying may be carried out using vacuum drying. For example, it may be carried out at a temperature of 40° C. to 90° C. and a pressure of 2.0 torr or less.

As a result, the impurities generated in the step of obtaining the diamine hydrochloride composition may be removed together with the first organic solvent. Thus, the process may further comprise removing the impurities generated in the step of obtaining the diamine hydrochloride composition together with the first organic solvent. Impurities are generated in the reaction for preparing the diamine hydrochloride composition and are contained in the first organic solvent. Such impurities may be removed by the step of removing the first organic solvent, whereby the purity of the product may be increased.

According to the above process, a diamine is reacted with an aqueous hydrochloric acid solution, which is then subjected to additional treatment such as precipitation, filtration, drying, and washing, whereby a solid diamine hydrochloride composition can be obtained with high purity. In contrast, in the conventional process in which a diamine is reacted with hydrogen chloride gas in an organic solvent, a slurry of a diamine hydrochloride is obtained, which is not readily purified.

The yield of the diamine hydrochloride composition thus obtained may be 50% or more, 65% or more, 80% or more, 85% or more, or 90% or more, specifically 85% to 95% or 88% to 92%.

Meanwhile, the organic layer can be separated from the reactant and recycled as an organic solvent. Thus, the recovery rate of the first organic solvent may be 80% or more, 85% or more, or 90% or more, specifically 80% to 95% or 80% to 82%.

Diamine Hydrochloride Composition

In the process for preparing a diamine hydrochloride as described above, the diamine is easily deteriorated by temperature and humidity due to its high reactivity and pH, so that the b* value according to the CIE color coordinate of the diamine hydrochloride composition may be increased. In particular, if a diamine hydrochloride composition having a b* value of a certain level or more is used to prepare a diisocyanate composition, the color and haze may be deteriorated, and it may have an impact on the stria, transmittance, yellow index, and refractive index of the final optical lens. In addition, if distillation is carried out several times in order to make a discolored diisocyanate composition colorless and transparent, it may cause a loss in yield, thereby decreasing the economic efficiency.

According to the above embodiment, however, the b* value according to the CIE color coordinate of the diamine hydrochloride composition in water may be adjusted, so that it is possible to enhance the optical characteristics of a diisocyanate composition and an optical lens.

The diamine hydrochloride composition prepared by the process according to the above embodiment has a b* value according to the CIE color coordinate of 1.2 or less when dissolved in water at a concentration of 8% by weight. For example, the b* value according to the CIE color coordinate may be 1.0 or less or 0.8 or less. Specifically, the b* value according to the CIE color coordinate may be 0.1 to 1.2, 0.1 to 1.0, 0.1 to 0.8, or 0.3 to 1.0.

In order to adjust the b* value of the diamine hydrochloride composition, an aqueous hydrochloric acid solution having a content of Fe ions at a certain level or less may be used as a raw material. For example, the content of Fe ions in the aqueous hydrochloric acid solution used for preparing the diamine hydrochloride composition may be 0.5 ppm or less. Specifically, the content of Fe ions in the aqueous hydrochloric acid solution may be 0.3 ppm or less or 0.2 ppm or less. More specifically, the content of Fe ions in the aqueous hydrochloric acid solution may be 0.001 ppm to 0.5 ppm or 0.1 ppm to 0.3 ppm.

Alternatively, the b* value according to the CIE color coordinate of the diamine hydrochloride composition may be adjusted by washing it with a solvent having a polarity index of 9.8 or less. That is, the process for preparing a diamine hydrochloride composition adopted in the above embodiment comprises washing the composition comprising a diamine hydrochloride with a solvent having a polarity index of 9.8 or less to adjust the b* value according to the CIE color coordinate to 1.2 or less when dissolved in water at a concentration of 8% by weight.

In such event, the solvent having a polarity index of 9.8 or less may comprise dichloromethane, and other solvents may be used. In addition, the temperature of the solvent having a polarity index of 9.8 or less may be 0° C. to 5° C.

The diamine hydrochloride composition obtained by the above process mainly comprises a diamine hydrochloride, and the content of the diamine hydrochloride may be 90% by weight to 99.9% by weight based on the total weight of the composition. In such event, the diamine hydrochloride may contain two of HCl bonded to the two terminal amine groups of the diamine.

In addition, the diamine hydrochloride composition may comprise Fe ions, and the content of Fe ions may be 10 ppm or less based on the total weight of the diamine hydrochloride composition.

In addition, the content of water in the diamine hydrochloride composition thus obtained may be 5% or less. If it exceeds 5%, the physical properties of the lens finally prepared are not good.

In addition, the content of water in the diamine hydrochloride composition obtained in the previous step may be adjusted, and it is then introduced to the subsequent reaction. For example, the process may further comprise adjusting the content of water in the diamine hydrochloride composition obtained in the previous step to 700 ppm or less.

The content of water in the diamine hydrochloride composition may be adjusted to, for example, 500 ppm or less, 300 ppm or less, 200 ppm or less, 100 ppm or less, or 50 ppm or less. Specifically, the diamine hydrochloride composition in which the content of water has been adjusted may have a content of water of 100 ppm or less or 50 ppm or less.

The content of water in the diamine hydrochloride composition may be adjusted in advance before it is introduced to the subsequent reaction. That is, the process may further comprise measuring the content of water in the diamine hydrochloride composition before it is introduced to the subsequent reaction.

The content of water in the diamine hydrochloride composition may be adjusted is through at least one of washing and drying.

As an example, the content of water in the diamine hydrochloride composition may be adjusted by washing it with a solvent having a polarity index of 3.9 to 5.7. If the solvent used for washing as described above has a polarity index of 3.9 or more, it is miscible with water and effective in removing water. In addition, if it has a polarity index of 5.7 or less, it does not dissolve triphosgene, thereby increasing the yield.

In addition, if the solvent used for washing has a boiling point of 85° C. or lower, it reduces the residual solvents after drying, thereby enhancing the purity and yield of the product. For example, the boiling point of the solvent used for washing may be 30° C. to 85° C.

Specifically, the solvent used for washing may include at least one selected from the group consisting of tetrahydrofuran (THF), ethyl acetate, methyl acetate, methyl ethyl ketone, and acetone. More specifically, the solvent used for washing may include at least one selected from tetrahydrofuran and acetone.

The content of water in the diamine hydrochloride composition may be adjusted by drying it under a reduced pressure. For example, the content of water in the diamine hydrochloride composition may be adjusted by drying under the conditions of a temperature of 40° C. to 90° C. and a pressure of 0.01 torr to 100 torr.

The drying step may be performed after the above washing is first performed. That is, the content of water in the diamine hydrochloride composition, after the washing, may be further adjusted by drying under the conditions of a temperature of 40° C. to 90° C. and a pressure of 0.01 torr to 100 torr.

In the diamine hydrochloride composition, after the drying, the content of the residual solvents used in the washing may be less than 500 ppm or less than 300 ppm, specifically less than 100 ppm.

Preparation of a Diisocyanate Composition

Next, the diamine hydrochloride composition is reacted with a triphosgene composition to obtain a diisocyanate composition. The reaction of the diamine hydrochloride composition with a triphosgene composition may be carried out in a second organic solvent.

The following Reaction Scheme 2 shows an example of the reaction in this step.

[Reaction Scheme 2]

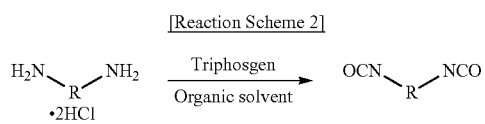

In the above scheme, R comprises an aromatic ring, an aliphatic ring, an aliphatic chain, and the like. As a specific example, R may be xylylene, norbornene, hydrogenated xylylene, isophorone, or hexamethylene, but it is not limited thereto.

Specifically, the diamine hydrochloride composition prepared above is introduced to a second organic solvent, reacted with a triphosgene (BTMC, bis(trichloromethyl) carbonate) composition, and then filtered and distilled to obtain a diisocyanate composition.

Specifically, the second organic solvent may be at least one selected from the group consisting of benzene, toluene, ethylbenzene, chlorobenzene, monochlorobenzene, 1,2-dichlorobenzene, dichloromethane, 1-chloro-n-butane, 1-chloro-n-pentane, 1-chloro-n-hexane, chloroform, carbon tetrachloride, n-pentane, n-hexane, n-heptane, n-octane, cyclohexane, cyclopentane, cyclooctane, and methylcyclohexane.

The amount (weight) of the second organic solvent introduced may be 1 to 5 times the weight of the diamine hydrochloride composition. If the introduced amount is within the above range, it is possible to prevent the use of excessive organic solvents while the yield of the final diisocyanate is high. Specifically, the second organic solvent may be introduced to the reaction in an amount of 2 to 5 times, or 3 to 5 times, the weight of the diamine hydrochloride composition.

The reaction temperature of the diamine hydrochloride composition and the triphosgene composition is 115° C. or higher, so that the reaction between the diamine hydrochloride and the triphosgene composition is carried out more smoothly, which may be advantageous for increasing the yield and shortening the reaction time. In addition, if the reaction temperature of the diamine hydrochloride composition and the triphosgene composition is 160° C. or less, it is possible to suppress the generation of impurities such as tar when the final diisocyanate is produced. For example, the reaction temperature of the diamine hydrochloride composition and the triphosgene composition may be 115° C. to 160° C., 15° C. to 130° C., or 130° C. to 160° C.

In addition, if the reaction temperature of the diamine hydrochloride composition and the triphosgene composition is 130° C. or lower, it may be more advantageous for suppressing impurities containing chlorine (e.g., chloromethylbenzyl isocyanate, 1,3-bis(chloromethyl)benzene, and the like). Specifically, the reaction temperature of the diamine hydrochloride composition and the triphosgene composition may be 115° C. to 130° C. More specifically, the reaction temperature of the diamine hydrochloride composition and the triphosgene composition may be 115° C. to 120° C.

The reaction of the diamine hydrochloride composition with the triphosgene composition may be carried out for 5 hours to 100 hours. If the reaction time is within the above range, the reaction time is not excessive, and the production of unreacted materials due to the generation of phosgene can be minimized. Specifically, the reaction of the diamine hydrochloride composition with the triphosgene composition may be carried out for 15 hours to 40 hours, 20 hours to 35 hours, or 24 hours to 30 hours.

As a specific example, the reaction of the diamine hydrochloride composition with the triphosgene composition may be carried out at a temperature of 115° C. to 160° C. for 5 hours to 100 hours.

The diamine hydrochloride composition and the triphosgene composition may be introduced to the reaction at an equivalent ratio of 1:1 to 5. When the equivalent ratio is within the above range, the reaction efficiency is high, and it is possible to prevent an increase in the reaction time due to an excessive introduction. Specifically, the diamine hydrochloride composition and the triphosgene composition may be introduced to the reaction at an equivalent ratio of 1:1.5 to 4 or 1:2 to 2.5.

The reaction of the diamine hydrochloride composition and the triphosgene composition may sequentially comprise mixing the diamine hydrochloride composition with the second organic solvent to obtain a first solution; mixing the triphosgene composition with the second organic solvent to obtain a second solution; and introducing the second solution to the first solution and stirring them. In such event, the introduction of the second solution and stirring may be carried out at a temperature of 115° C. to 160° C. In addition, the introduction of the second solution may be divided into two or more times for a total of 25 hours to 40 hours. In addition, here, the time for each introduction may be 5 hours to 25 hours or 10 hours to 14 hours. In addition, the time for further reaction by stirring after the introduction may be 2 hours to 5 hours or 3 hours to 4 hours.

Alternatively, the reaction of the diamine hydrochloride composition and the triphosgene composition may sequentially comprise (2a) introducing the second organic solvent to a second reactor; (2b) further introducing the diamine hydrochloride composition to the second reactor and stirring them; and (2c) further introducing the triphosgene composition to the second reactor and stirring them. In such event, the introduction of the triphosgene composition in step (2c) may be carried out by introducing a solution in which the triphosgene composition is dissolved in the same solvent as the second organic solvent to the reactor as divided into two or more times at a temperature of 115° C. to 160° C. for a total of 25 hours to 40 hours. In such event, the time for each introduction of the triphosgene composition may be 5 hours to 25 hours or 10 hours to 14 hours. In addition, the time for further reaction by stirring after the introduction of the triphosgene composition may be 2 hours to 5 hours or 3 hours to 4 hours.

Upon the reaction, the reaction resultant may be cooled at 90° C. to 110° C.

The resultant obtained through the reaction may be further subjected to separation, degassing, cooling, filtration, distillation, and the like.

For example, after the reaction, the reaction resultant may be subjected to degassing at 80° C. to 150° C. with the bubbling of nitrogen gas. In addition, after the degassing, it may be cooled to 10° C. to 30° C., and solids may be filtered off.

The diisocyanate composition may be obtained by distillation after the reaction of the diamine hydrochloride composition and the triphosgene composition.

The distillation may comprise distillation to remove the second organic solvent. For example, after the reaction, the reaction resultant may be distilled at 40° C. to 60° C. for 2 hours to 8 hours to remove the second organic solvent. The pressure during the distillation may be 2.0 torr or less, 1.0 torr or less, 0.5 torr or less, or 0.1 torr or less. In addition, the second organic solvent may be recovered and recycled through the distillation.

In addition, the distillation may comprise distilling the diisocyanate. For example, the distillation may comprise distillation of a diisocyanate at 80° C. to 160° C., specifically 100° C. to 130° C. If the distillation temperature is within the above range, it is more advantageous for preventing a deterioration in the physical properties of the final optical lens such as stria, cloudiness, and yellowing by effectively removing hydrolyzable chlorine compounds generated at high temperatures such as chloromethylbenzyl isocyanate (CBI) and 1,3-bis(chloromethyl)benzene. Specifically, the distillation may be carried out by setting the bottom temperature of the distiller to 100° C. to 130° C. For example, the distillation may be carried out by setting the reboiler temperature to 100° C. to 130° C.

In addition, the pressure during the distillation may be 2.0 torr or less, 1.0 torr or less, 0.5 torr or less, or 0.1 torr or less. Specifically, the distillation may comprise distillation of a diisocyanate at a temperature of 100° C. to 130° C. and a pressure of 2 torr or less.

In addition, the time for distillation of a diisocyanate may be 1 hour or longer, 2 hours or longer, or 3 hours or longer, and may be 10 hours or shorter or 5 hours or shorter. Specifically, the distillation of a diisocyanate may be carried out for 2 hours to 10 hours.

As a specific example, the diisocyanate composition may be obtained as a result of subjecting the resultant of the reaction of the diamine hydrochloride composition and the triphosgene composition to first distillation at 40° C. to 60° C. for 2 to 8 hours and second distillation at 80° C. to 160° C. for 2 to 10 hours.

The yield of the distillation of a diisocyanate may be 80% or more, specifically 85% or more, or 90% or more. In such event, the distillation yield may be calculated by measuring the amount of the diisocyanate composition upon the distillation relative to the theoretical amount of the diisocyanate composition produced from the amounts of the diamine hydrochloride composition introduced to the reaction with the triphosgene composition.

According to the process of the above embodiment, the reaction temperature range of the diamine hydrochloride composition and the triphosgene composition is controlled, whereby the crude diisocyanate composition before purification may contain very little impurities. Specifically, the diisocyanate composition may contain 99.0% by weight or more of the diisocyanate before the distillation of a diisocyanate. In addition, the diisocyanate composition may contain 99.9% by weight or more of the diisocyanate after the distillation of a diisocyanate.

In addition, the content of aromatic compounds having a halogen group in the diisocyanate composition may be 1,000 ppm or less.

In addition, the yield of the diisocyanate composition finally obtained may be 80% or more, 85% or more, or 90% or more.

Triphosgene Composition

The triphosgene composition used in the process according to the above embodiment may comprise triphosgene and a decomposition product of triphosgene.

Here, the content of the decomposition product of triphosgene in the triphosgene composition is less than 1% by weight based on the total weight of the triphosgene composition.

For example, the content of the decomposition product of triphosgene in the triphosgene composition may be 0.9% by weight or less, 0.7% by weight or less, or 0.5% by weight or less. Specifically, the content of the decomposition product of triphosgene in the triphosgene composition may be 0.01% by weight to 0.9% by weight or 0.01% by weight to 0.7% by weight. More specifically, the content of the decomposition product of triphosgene in the triphosgene composition may be 0.01% by weight to 0.5% by weight.

In addition, the content of triphosgene in the triphosgene composition is 50% by weight or more, 70% by weight or more, 80% by weight or more, or 90% by weight or more, based on the total weight of the triphosgene composition. For example, the content of triphosgene in the triphosgene composition may be 70/by weight to 99.9% by weight or 80% by weight to 99.9% by weight. Specifically, the content of triphosgene in the triphosgene composition may be 90% by weight to 99.9% by weight.

The decomposition product of triphosgene refers to a compound produced by the decomposition of triphosgene for various reasons. For example, triphosgene is in part decomposed by various causes such as air metal salt, silica gel, dust, heat, and the like to generate phosgene, carbon dioxide, and carbon tetrachloride (see the following Reaction Scheme 3).

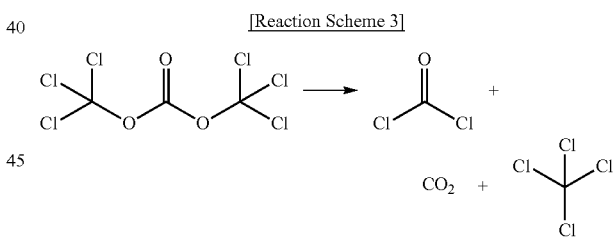

[Reaction Scheme 3]

As a result, the triphosgene composition may comprise phosgene, carbon dioxide, carbon tetrachloride, and the like. In particular, if a triphosgene composition containing carbon tetrachloride in a certain amount or more is used to prepare a diisocyanate composition, the color and haze may be deteriorated, and it may have an impact on the stria, transmittance, yellow index, and refractive index of the final optical lens.

However, according to the above embodiment, the content of a decomposition product such as carbon tetrachloride in triphosgene used to prepare a diisocyanate composition is adjusted to less than 1% by weight, whereby it is possible to enhance the characteristics of the final optical lens. For example, the content of carbon tetrachloride in the triphosgene composition may be 0.9% by weight or less, 0.7% by weight or less, or 0.5% by weight or less. Specifically, the content of carbon tetrachloride in the triphosgene composition may be 0.01% by weight to 0.9% by weight or 0.01% by weight to 0.7% by weight. More specifically, the content of carbon tetrachloride in the triphosgene composition may be 0.01% by weight to 0.5% by weight.

In particular, the content of the decomposition product of triphosgene in the triphosgene composition may be adjusted by washing it with diethyl ether at 5° C. or lower. That is, the process for preparing a triphosgene composition adopted in the above embodiment comprises washing a composition comprising triphosgene with diethyl ether at 5oC or lower to adjust the content of a decomposition product of triphosgene in the triphosgene composition to less than 1% by weight based on the total weight of the composition.

Alternatively, if the triphosgene composition contains less than 1% by weight of a decomposition product of triphosgene without such washing, it may be used for preparing a diisocyanate composition without any other treatment.

In addition, the triphosgene composition used in the process according to the above embodiment has a b* value according to the CIE color coordinate of 1.2 or less when dissolved in orthodichlorobenzene at a concentration of 8% by weight. For example, the b* value according to the CIE color coordinate may be 1.0 or less, specifically 0.8 or less. More specifically, the b* value according to the CIE color coordinate may be 0.1 to 1.2, 0.1 to 1.0, 0.3 to 1.2, or 0.1 to 0.8.

The b* value according to the CIE color coordinate of the triphosgene composition may be adjusted by washing it with a 10% to 30/sodium chloride solution.

Triphosgene may react with moisture in the air during storage to generate phosgene, which in turn may react with moisture in the air to increase the b* value according to the CIE color coordinate of triphosgene. If a triphosgene composition having a b* value of a certain level or more is used to prepare a diisocyanate composition, the color and haze may be deteriorated, and it may have an impact on the stria, transmittance, yellow index, and refractive index of the final optical lens. In addition, if distillation is carried out several times in order to make a discolored diisocyanate composition colorless and transparent, it may cause a loss in yield, thereby decreasing the economic efficiency.

According to the above embodiment, however, the b* value according to the CIE color coordinate of the triphosgene composition in an organic solvent may be adjusted, so that it is possible to enhance the color and haze of a diisocyanate composition prepared using the same.

The b* value according to the CIE color coordinate of the triphosgene composition may be adjusted by washing it with a 10% to 30% sodium chloride solution. That is, the process for preparing a triphosgene composition used in the above embodiment comprises washing the composition comprising triphosgene with a 10% to 30% sodium chloride solution to adjust the b* value according to the CIE color coordinate to 1.2 or less when dissolved in orthodichlorobenzene at a concentration of 8% by weight.

In addition, according to the above embodiment, the content of water in triphosgene used in the reaction of the diamine hydrochloride composition and triphosgene is 200 ppm or less.

The content of water in the triphosgene may be adjusted in advance before it is introduced to the reaction. Thus, the process may further comprise measuring the content of water in the triphosgene before it is introduced to the reaction.

As a result of the measurement, if the content of water in triphosgene is 200 ppm or less, it may be introduced to the reaction as it is. However, if the content of water in the triphosgene exceeds 200 ppm, the content of water may be adjusted.

For example, the content of water in the triphosgene may be adjusted through at least one further step of washing and drying.

As an example, the triphosgene may be washed with a solvent having a polarity index of 3.9 to 5.7 before it is introduced to the reaction. If the solvent used for washing as described above has a polarity index of 3.9 or more, it is miscible with water and effective in removing water. In addition, if it has a polarity index of 5.7 or less, it does not dissolve triphosgene, thereby increasing the yield.

In addition, if the solvent used in the washing does not have a hydroxyl group or an amine group, it is possible to enhance the purity and yield of the product by preventing side reactions with triphosgene.

In addition, if the solvent used for washing has a boiling point of 85° C. or lower, it reduces the residual solvents after drying, thereby enhancing the purity and yield of the product. For example, the boiling point of the solvent used for washing may be 30° C. to 85° C.

Specifically, the solvent used for washing may include at least one selected from the group consisting of tetrahydrofuran (THF), ethyl acetate, methyl acetate, methyl ethyl ketone, and acetone. More specifically, the solvent used for washing may include at least one selected from tetrahydrofuran and acetone.

In addition, the content of water in the triphosgene may be adjusted by drying it under a reduced pressure. For example, the triphosgene may be dried for 2 hours to 10 hours under the conditions of a temperature of 20° C. to 60° C. and a pressure of 0.01 torr to 100 torr before it is introduced to the reaction.

The drying step may be performed after the above washing is first performed. That is, the triphosgene, after the washing, may be further dried under the conditions of a temperature of 20° C. to 60° C. and a pressure of 0.01 torr to 100 torr.

In the triphosgene, after the drying, the content of the residual solvents used in the washing may be less than 100 ppm.

In addition, the content of water in the triphosgene may be 100 ppm or less, or 50 ppm or less, after the further step (i.e., at least one of washing and drying).

As described above, the content of water in triphosgene is adjusted within a specific range, so that the formation of urea during the phosgenation reaction can be suppressed, thereby preventing a deterioration in the physical properties of the final optical lens such as stria, cloudiness, and yellowing.

Adjustment of the Content of Water in the Second Organic Solvent

In addition, the content of water in the organic solvent (i.e., second organic solvent) used in the reaction of the diamine hydrochloride composition and triphosgene may be adjusted.

For example, the content of water in the second organic solvent used in the reaction of the diamine hydrochloride composition and triphosgene may be 200 ppm or less.

The content of water in the second organic solvent may be adjusted in advance before it is introduced to the reaction. Thus, the process may further comprise measuring the content of water in the second organic solvent before it is introduced to the reaction.

As a result of the measurement, if the content of water in the second organic solvent is 200 ppm or less, it may be introduced to the reaction as it is. However, if the content of water in the second organic solvent exceeds 200 ppm, the content of water may be adjusted.

Specifically, the content of water in the second organic solvent may be adjusted by dehydration under a reduced pressure. The pressure during the dehydration may be 2.0 torr or less, 1.0 torr or less, 0.5 torr or less, or 0.1 torr or less. The temperature during the dehydration is 20° C. or higher, which is advantageous for removing sufficient water. In addition, it is 40° C. or lower, which is advantageous for increasing the dehydration yield by suppressing the evaporation of the solvent during the dehydration step. Thus, the temperature during the dehydration may be adjusted to 20° C. to 40° C. In addition, the time for the dehydration may be 1 hour or longer or 2 hours or longer, and 5 hours or shorter or 3 hours or shorter. As a specific example, the dehydration may be performed for 1 hour to 3 hours under a pressure of 0.5 torr or less. The equipment and method used for the dehydration are not particularly limited. For example, the dehydration may be performed with a vacuum pump with stirring.

The dehydration yield may be 80% or more, specifically 85% or more, or 90% or more.

In addition, the content of water in the second organic solvent may be 100 ppm or less after the dehydration.

As described above, the content of water in the organic solvent used in the reaction of a diamine hydrochloride composition and triphosgene is adjusted within a specific range, so that the formation of urea during the phosgenation reaction can be suppressed, thereby preventing a deterioration in the physical properties of the final optical lens such as stria, cloudiness, and yellowing. In addition, the content of water contained in the organic solvent during the reaction, transport, and storage is reduced. Even if the organic solvent is recovered after the reaction and then recycled for the next reaction, the quality of the product may not be deteriorated.

Diisocyanate Composition

The diisocyanate composition prepared using a diamine hydrochloride composition and a triphosgene composition as described above may be improved in terms of the color and haze.

The diisocyanate composition may have an APHA (American Public Health Association) color value of 20 or less or 10 or less. Specifically, the diisocyanate composition may have an APHA color value of 1 to 20 or 1 to 10.

In addition, the diisocyanate composition has a b* value according to the CIE color coordinate of 1.5 or less or 1.2 or less. Specifically, the b* value according to the CIE color coordinate of the diisocyanate composition may be 1.0 or less. More specifically, the b* value according to the CIE color coordinate of the diisocyanate composition may be 0.1 to 1.2, 0.1 to 1.0, 0.3 to 1.2, or 0.1 to 0.8.

In addition, the diisocyanate composition may have a haze of 10% or less, 5% or less, or 3% or less.

Thus, the diisocyanate thus prepared according to the embodiment can be applied to a plastic optical lens of high quality.

In addition, the content of Fe ions in the diisocyanate composition may be 10 ppm or less, 5 ppm or less, 2 ppm or less, or 1 ppm or less. Specifically, the content of Fe ions in the diisocyanate composition may be 0.2 ppm or less.

In addition, the content of a diisocyanate in the diisocyanate composition may be 90% by weight or more, 95% by weight or more, or 99.5% by weight or more, specifically 90% to 99.9% by weight.

In addition, the diisocyanate composition may further comprise benzyl isocyanate, methylbenzyl isocyanate, cyanobenzyl isocyanate, and the like. The total content of these components may be about 1% by weight or less.

The diisocyanate composition may comprise xylylene diisocyanate or other diisocyanates used in the preparation of optical lenses. Specifically, it may comprise at least one selected from the group consisting of orthoxylylene diisocyanate (o-XDI), metaxylylene diisocyanate (m-XDI), paraxylylene diisocyanate (p-XDI), norbornene diisocyanate (NBDI), hydrogenated xylylene diisocyanate (H6XDI), isophorone diisocyanate (IPDI), and hexamethylene diisocyanate (HDI).

According to the process of the above embodiment, the yield of a diisocyanate is high, the recycling rate of organic solvents is excellent, it is environmentally friendly since highly toxic phosgene gas is not used, it is possible to react at atmospheric pressure, and a separate apparatus for pressurization or rapid cooling is not required.

Measurement of the Color and Transparency of a Reaction Solution

The step of obtaining a diisocyanate composition from the diamine hydrochloride composition and the triphosgene composition may comprise (aa) reacting the diamine hydrochloride composition with triphosgene in a second organic solvent in a reactor to obtain a reaction solution; (ab) measuring the color and transparency of the reaction solution; and (ac) obtaining a diisocyanate composition from the reaction solution.

In the reaction of the diamine hydrochloride composition and the triphosgene composition, the color and transparency of the reaction solution may be measured to adjust the reaction conditions.

For example, in the reaction of metaxylylenediamine hydrochloride and the triphosgene composition to obtain metaxylylene diisocyanate, the reaction solution at the beginning of the reaction may be opaque colorless or white, and the reaction solution at the time when the reaction is ordinarily completed may be transparent or close to transparent in a light brown color.

For example, in the step of measuring the color and transparency of the reaction solution, the reaction solution may have a transparent light brown color.

Specifically, the reaction solution may have an $L^*$ value of 45 to 60, an $a^*$ value of 3 to 15, and a $b^*$ value of 15 to 30 in the CIE-LAB color coordinate. More specifically, the reaction solution may have an $L^*$ value of 50 to 55, an $a^*$ value of 5 to 10, and a $b^*$ value of 20 to 25 in the CIE-LAB color coordinate.

In addition, the reaction solution may have a transmittance of 60% or more, 70% or more, 80/or more, or 90% or more, for light having a wavelength of 550 nm. In addition, the reaction solution may have a haze of 20% or less, 10% or less, 5% or less, or 3% or less. Specifically, the reaction solution may have a transmittance of 70% or more for light having a wavelength of 550 nm and a haze of 10% or less. More specifically, the reaction solution may have a transmittance of 80% or more for light having a wavelength of 550 nm and a haze of 5% or less.

On the other hand, if the reaction of the metaxylylenediamine hydrochloride and the triphosgene composition is not completed, the reaction solution may be opaque or have a precipitate, and the color may be pale, white, or colorless. In addition, if side reactions take place to a significant extent, the reaction solution may be opaque or may have a color other than light brown, for example, a dark brown or dark color.

The reaction of the diamine hydrochloride composition and the triphosgene composition may be carried out simultaneously with the step of measuring the color and transparency of the reaction solution.

That is, while the reaction of the diamine hydrochloride composition and the triphosgene composition is being carried out, the color and transparency of the reaction solution may be measured in real time.

In addition, for more accurate measurement, a part of the reaction solution may be collected to precisely measure the color and transparency thereof. For example, the measurement of the color and transparency of the reaction solution may be carried out by collecting a part of the reaction solution and measuring the color and transparency of the collected reaction solution.

In such event, the reaction equivalent, reaction temperature, or reaction time may be adjusted according to the color and transparency of the reaction solution. For example, the timing for terminating the reaction may be determined according to the color and transparency of the reaction solution. Specifically, the timing for terminating the reaction may come after when the reaction solution turns a transparent light brown color.

As an example, the reactor may have a viewing window, and the measurement of the color and transparency of the reaction solution may be carried out through the viewing window.

The reactor is connected to one or more stages of condensers. Once the gas generated in the reactor has been transferred to the one or more stages of condensers, the second organic solvent present in the gas may be condensed and recycled to the reactor.

The one or more stages of condensers are connected to a first scrubber and a second scrubber. The gas transferred from the reactor to the one or more stages of condensers contains hydrogen chloride gas and phosgene gas, the first scrubber may dissolve the hydrogen chloride gas in water to produce an aqueous solution, and the second scrubber may neutralize the phosgene gas with an aqueous NaOH solution.

In addition, the reactor is connected to one or more stages of distillers. The reaction solution is transferred to the one or more stages of distillers, and the one or more stages of distillers may separate the diisocyanate composition and the second organic solvent from the reaction solution.

The separated second organic solvent may be recycled for the reaction of the diamine hydrochloride composition and the triphosgene composition.

FIG. 2 shows an example of the process equipment for the reaction of a diamine hydrochloride composition and a triphosgene composition.

First, a first tank (T-1) is charged with a second organic solvent and a triphosgene composition, and the temperature is maintained to be constant by refluxing hot water. The inside of a reactor (R-1) is purged with nitrogen, a second organic solvent is introduced thereto with stirring, a diamine hydrochloride composition is slowly introduced thereto, and they are stirred while the internal temperature of the reactor is maintained to be constant.

Thereafter, the triphosgene composition in the second organic solvent is gradually introduced to the reactor (R-1) from the first tank (T-1). The introduction of the triphosgene composition in the second organic solvent is carried out at a time or divided into two or more times. At that time, stirring is performed while the internal temperature of the reactor (R-1) is maintained to be constant. Upon completion of the introduction, an additional reaction is carried out while stirring is performed for a certain period of time. As an example, the color and transparency of the reaction solution are monitored with the naked eyes through a viewing window (G-1) provided in the reactor (R-1). As another example, the color and transparency of the reaction solution are measured with an optical device through the viewing window (G-1) provided in the reactor (R-1). The optical device may include a digital camera, a spectrometer, and optical analysis equipment.

The gas (second organic solvent, hydrogen chloride, phosgene, and the like) present inside the reactor (R-1) is transferred to a first condenser (C-1). In the first condenser (C-1), the second organic solvent is firstly condensed by cooling and recycled to the reactor (R-1), and the remaining gas is transferred to a second condenser (C-2). In the second condenser (C-2), the second organic solvent is secondly condensed by cooling and recycled to the reactor (R-1), and the remaining gas is transferred to a third condenser (C-3). In the third condenser (C-3), the second organic solvent is thirdly condensed by cooling and recycled to the reactor (R-1).

Once the second organic solvent is removed while it passes through the multi-stage condensers as described above, the remaining gas (hydrogen chloride, phosgene, and the like) is transferred to a first scrubber (S-1). In the first scrubber (S-1), hydrogen chloride gas is dissolved in water to obtain an aqueous hydrochloric acid solution and stored in a second tank (T-2), and the remaining gas is transferred to a second scrubber (S-2). In the second scrubber (S-1), phosgene ($COCl_2$) gas may be neutralized with an aqueous sodium hydroxide solution stored in a third tank (T-3) and removed.

The reaction solution obtained from the reactor (R-1) is sequentially transferred to a first distiller (D-1) and a second distiller (D-2). While it undergoes first and second distillation, the diisocyanate composition and the second organic solvent are separated from the reaction solution.

The second organic solvent separated from the reaction solution may be transferred to, and stored in, a solvent recovery apparatus (V-1). Thereafter, it may be recycled for the reaction of the diamine hydrochloride composition and the triphosgene composition.

In addition, the diisocyanate composition separated from the reaction solution may be further subjected to filtration and drying to provide a final product.

[Process for the Preparation of an Optical Lens]

The diisocyanate composition prepared in the above embodiment may be combined with other components to prepare a composition for an optical material. That is, the composition for an optical material comprises a diisocyanate composition prepared according to the above embodiment and a thiol or an episulfide. The composition for an optical material may be used to prepare an optical material, specifically an optical lens. For example, the composition for an optical material is mixed and heated and cured in a mold to produce an optical lens. The process for preparing an optical lens or the characteristic thereof described below should be understood as a process for preparing various optical materials or the characteristic thereof that can be implemented using the diisocyanate composition according to the embodiment in addition to an optical lens.

The process for preparing an optical lens according to an embodiment comprises reacting a diamine hydrochloride composition with a triphosgene composition to obtain a diisocyanate composition; and mixing the diisocyanate composition with a thiol or an episulfide and polymerizing and curing the resultant in a mold, wherein the content of a decomposition product of triphosgene in the triphosgene composition is less than 1% by weight.

The process for preparing an optical lens according to another embodiment comprises reacting a diamine hydrochloride composition with a triphosgene composition to obtain a diisocyanate composition; and mixing the diisocyanate composition with a thiol or an episulfide and polymerizing and curing the resultant in a mold, wherein the triphosgene composition has a b* value according to the CIE color coordinate of 1.2 or less when dissolved in orthodichlorobenzene at a concentration of 8% by weight.

The process for preparing an optical lens according to still another embodiment comprises reacting a diamine with an aqueous hydrochloric acid solution to obtain a diamine hydrochloride composition; reacting the diamine hydrochloride composition with triphosgene to obtain a diisocyanate composition; and mixing the diisocyanate composition with a thiol or an episulfide and polymerizing and curing the resultant in a mold, wherein the content of water in the triphosgene is 200 ppm or less.

The thiol may be a polythiol containing two or more SH groups. It may have an aliphatic, alicyclic, or aromatic skeleton. The episulfide may have two or more thioepoxy groups. It may have an aliphatic, alicyclic, or aromatic skeleton.

Specific examples of the thiol include bis(2-mercaptoethyl) sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropanyl) sulfide, bis(2,3-dimercaptopropanyl) disulfide, 1,2-bis(2-mercaptoethylthio)-3-mercaptopropane, 1,2-bis(2-(2-mercaptoethylthio)-3-mercaptopropylthio)ethane, bis(2-(2-mercaptoethylthio)-3-mercaptopropyl) sulfide, bis(2-(2-mercaptoethylthio)-3-mercaptopropyl) disulfide, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaethritol tetrakis(2-mercaptoacetate), bispentaerythritol-ether-hexakis(3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis(mercaptodimethylthio)ethyl)-1,3-dithiane, 2,5-bismercaptomethyl-1,4-dithiane, bis(mercaptomethyl)-3,6,9-trithiaundecan-1,11-dithiol.

Preferably, the thiol may be 2-(2-mercaptoethylthio)propane-1,3-dithiol, 2,3-bis(2-mercaptoethylthio)propane-1-thiol, 2-(2,3-bis(2-mercaptoethylthio)propylthio)ethanethiol, 1,2-bis(2-mercaptoethylthio)-3-mercaptopropane, 1,2-bis(2-(2-mercaptoethylthio)-3-mercaptopropylthio)ethane, bis(2-(2-mercaptoethylthio)-3-mercaptopropyl) sulfide, 2-(2-mercaptoethylthio)-3-2-mercapto-3-[3-mercapto-2-(2-mercaptoethylthio)-propylthio]propylthio-propane-1-thiol, 2,2'-thiodiethanethiol, 4,14-bis(mercaptomethyl)-3,6,9,12,15-pentathiahectadecane-1,17-dithiol, 2-(2-mercaptoethylthio)-3-[4-(1-{4-[3-mercapto-2-(2-mercaptoethylthio)-propoxy]-phenyl}-1-methylethyl)-phenoxy]-propane-1-thiol, pentaerythritol tetrakis(3-mercaptopropionate), pentaerythritol mercaptoacetate, trimethanolpropanetrismercaptopropionate, glycerol trimercaptopropionate, dipentaerythritol hexamercaptopropionate, or 2,5-bismercaptomethyl-1,4-dithiane.

The thiol may be any one or two or more of the exemplary compounds, but it is not limited thereto.

In addition, specific examples of the episulfide include bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, 1-(β-epithiopropylthio)-2-[[2-(2-β-epithiopropylthioethyl)thioethyl]thio]ethane, tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethy)-5-[(2-β-epithiopropylthioethyl)thiomethyl]-3,7-ditianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, 1,11-bis(β-epithiopropylthio)-4,7-bis(β-epithiopropylthiomethyl)-3,6,9-trithiaundecane, 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl] sulfide, 2,5-bis(β-epithiopropylthiomethyl)-1,4-dithiane, 2,5-bis(β-epithiopropylthioethylthiomethyl)-1,4-dithiane, 1,3-bis(β-epithiopropylthio)benzene, 1,4-bis(β-epithiopropylthio)benzene, 1,3-bis(β-epithiopropylthiomethyl)benzene, 1,4-bis(β-epithiopropylthiomethyl)benzene, bis[4-(β-epithiopropylthio)phenyl]methane, 2,2-bis[4-(β-epithiopropylthio)phenyl]propane, bis[4-(β- epithiopropylthio)pheny]sulfide, bis[4-(β-epithiopropylthio) phenyl] sulfone, and 4,4'-bis(β-epithiopropylthio)biphenyl.

The episulfide may be any one or two or more of the exemplary compounds, but it is not limited thereto. In addition, the episulfide may be a compound in which at least one of the hydrogens of its thioepoxy group is substituted with a methyl group.

The composition for an optical material may comprise the diisocyanate composition and the thiol or episulfide in a mixed state or in a separated state. That is, in the composition, they may be in a state of being compounded in contact with each other or separated from each other so as not to contact each other.

The composition for an optical material may comprise the thiol or episulfide and the diisocyanate composition at a weight ratio of 2:8 to 8:2, 3:7 to 7:3, or 4:6 to 6:4.

A catalyst, a chain extender, a crosslinking agent, an ultraviolet stabilizer, an antioxidant, an anti-coloring agent, a dye, a filler, a release agent, and the like may be further added depending on the purpose when the composition for an optical material and an optical lens are prepared.

The thiol or episulfide is mixed with a diisocyanate composition and other additives, which is defoamed, injected into a mold, and gradually polymerized while the temperature is gradually elevated from low to high temperatures. The resin is cured by heating to prepare an optical lens.

The polymerization temperature may be, for example, 20° C. to 150° C., particularly 25° C. to 120° C. In addition, a reaction catalyst, which is conventionally used in the production of polythiourethane, may be employed in order to control the reaction rate. Specific examples of the reaction catalyst are as exemplified above.

In addition, if required, the optical lens thus prepared may be subjected to physical or chemical treatment such as anti-reflection coating, hardness, enhancements in abrasion resistance and chemical resistance, anti-fogging, surface polishing, antistatic treatment, hard coat treatment, anti-reflection treatment, and dyeing treatment.

The optical lens prepared by the above process has excellent optical properties such as transparency, refractive index, and yellow index. For example, the optical lens may have a refractive index of 1.55 or more, specifically a refractive index of 1.55 to 1.77. Alternatively, the optical lens may have a refractive index of 1.6 or more, specifically a refractive index of 1.6 to 1.7.

In addition, the optical lens may have an Abbe number of 30 to 50, specifically 30 to 45 or 31 to 40. In addition, the optical lens may have a light transmittance of 80% or more, 85% or more, or 87% or more, which may be a total light transmittance.

In addition, the optical lens may have a yellow index (Y.I.) of 30 or less, 25 or less, or 20 or less, for example, 1 to 25 or 10 to 20. Specifically, the optical lens may have a transmittance of 85% or more and a yellow index of 20 or less.

MODE FOR CARRYING OUT THE INVENTION

Hereinafter, more specific embodiments are illustrated, but the present invention is not limited thereto.

Preparation of a Diamine Hydrochloride Composition

Example A1

A 5-liter, 4-neck reactor was charged with 963.5 g (9.25 moles) of an aqueous solution of 35% hydrochloric acid, followed by lowering the internal temperature of the reactor to 15° C. with stirring. While the temperature of the reactor was maintained at 50° C., 600.0 g (4.4 moles) of metaxylylenediamine (m-XDA) was introduced for 1 hour. Upon completion of the introduction, the internal temperature of the reactor was lowered to 10° C., and it was stirred for 1 hour. Thereafter, 1,200.0 g of diethyl ether ($Et_2O$) as an organic solvent was introduced, and the internal temperature of the reactor was lowered to −5° C., followed by stirring for 1 hour. Upon completion of the reaction, it was subjected to vacuum filtration using a filter, and the filtered diethyl ether was recovered for reuse. The recovery rate of the diethyl ether was 73%. Upon the vacuum filtration, a metaxylylenediamine (m-XDA) hydrochloride composition was obtained. In order to remove the residual organic solvent and water, drying was performed under the conditions of a reactor external temperature of 90° C. and a vacuum pump of 0.1 Torr to obtain a final metaxylylenediamine (m-XDA) hydrochloride composition. The m-XDA hydrochloride composition thus obtained was in a solid form of a pale yellow, the yield was 88%, and the water content was 2%.

Example A2

A 5-liter, 4-neck reactor was charged with 986.5 g (9.47 moles) of an aqueous solution of 35% hydrochloric acid, followed by lowering the internal temperature of the reactor to 15° C. with stirring. While the temperature of the reactor was maintained at 50° C., 600.0 g (4.4 moles) of m-XDA was introduced for 1 hour. Upon completion of the introduction, the internal temperature of the reactor was lowered to 10° C., and it was stirred for 1 hour. Thereafter, 1,260 g of isopropanol (i-PrOH) as an organic solvent was introduced, and the internal temperature of the reactor was lowered to −5° C., followed by stirring for 1 hour. Upon completion of the reaction, it was subjected to vacuum filtration using a filter, and the filtered isopropanol was recovered for reuse. Here, the recovery rate of the isopropanol was 75%. Upon the vacuum filtration, a m-XDA hydrochloride composition was obtained. In order to remove the residual organic solvent and water, drying was performed under the conditions of a reactor external temperature of 90° C. and a vacuum pump of 0.1 Torr to obtain a final m-XDA hydrochloride composition. The m-XDA hydrochloride composition thus obtained was in a solid form of a pale yellow, the yield was 88%, and the water content was 2%.

Example A3

A 5-liter, 4-neck reactor was charged with 1,009.4 g (9.69 moles) of an aqueous solution of 35% hydrochloric acid, followed by lowering the internal temperature of the reactor to 15° C. with stirring. While the temperature of the reactor was maintained at 50° C., 600.0 g (4.4 moles) of m-XDA was introduced for 1 hour. Upon completion of the introduction, the internal temperature of the reactor was lowered to 10° C., and it was stirred for 1 hour. Thereafter, 1,320 g of tetrahydrofuran was introduced, and the internal temperature of the reactor was lowered to −5° C., followed by stirring for 1 hour. Upon completion of the reaction, it was subjected to vacuum filtration using a filter, and the filtered tetrahydrofuran was recovered for reuse. The recovery rate of the tetrahydrofuran was 82%. Upon the vacuum filtration, a m-XDA hydrochloride composition was obtained. In order to remove the residual solvent and water, drying was performed under the conditions of a reactor external temperature of 90° C. and a vacuum pump of 0.1 Torr to obtain a final m-XDA hydrochloride composition. The m-XDA hydrochloride composition thus obtained was in a solid form of a pale yellow, the yield was 91%, and the water content was 3%.

Example A4

A 5-liter, 4-neck reactor was charged with 1,032.3 g (9.91 moles) of an aqueous solution of 35% hydrochloric acid, followed by lowering the internal temperature of the reactor to 15° C. with stirring. While the temperature of the reactor was maintained at 50° C., 600.0 g (4.4 moles) of m-XDA was introduced for 1 hour. Upon completion of the introduction, the internal temperature of the reactor was lowered to 10° C., and it was stirred for 1 hour. Thereafter, 1,440 g of isobutanol (i-BuOH) as an organic solvent was introduced, and the internal temperature of the reactor was lowered to −5° C., followed by stirring for 1 hour. Upon completion of the reaction, it was subjected to vacuum filtration using a filter, and the filtered isobutanol was recovered for reuse. The recovery rate of the isobutanol was 82%. Upon the vacuum filtration, a m-XDA hydrochloride composition was obtained. In order to remove the residual solvent and water, drying was performed under the conditions of a reactor external temperature of 90° C. and a vacuum pump of 0.08 Torr to obtain a final m-XDA hydrochloride composition. The m-XDA hydrochloride composition thus obtained was in a solid form of a pale yellow, the yield was 92%, and the water content was 3%.

Example A5

A 5-liter, 4-neck reactor was charged with 1055.4 g (10.13 moles) of an aqueous solution of 35% hydrochloric acid, followed by lowering the internal temperature of the reactor to 15° C. with stirring. While the temperature of the reactor was maintained at 50° C., 600.0 g (4.4 moles) of m-XDA was introduced for 1 hour. Upon completion of the introduction, the internal temperature of the reactor was lowered to 10° C., and it was stirred for 1 hour. Thereafter, 1,500 g of methyl ethyl ketone (MEK) as an organic solvent was introduced, and the internal temperature of the reactor was lowered to −5° C., followed by stirring for 1 hour. Upon completion of the reaction, it was subjected to vacuum filtration using a filter, and the filtered methyl ethyl ketone was recovered for reuse. The recovery rate of the methyl ethyl ketone was 82%. Upon the vacuum filtration, a m-XDA hydrochloride composition was obtained. In order to remove the residual solvent and water, drying was performed under the conditions of a reactor external temperature of 90° C. and a vacuum pump of 0.05 Torr to obtain a final m-XDA hydrochloride composition. The m-XDA hydrochloride composition thus obtained was in a solid form of a pale yellow, the yield was 92%, and the water content was 1%.

Example A6

Reactor 1 was charged with 1,009.4 g (9.46 moles) of an aqueous solution of 35% hydrochloric acid, followed by lowering the internal temperature of Reactor 1 to 15° C. with stirring. While the temperature of Reactor 1 was maintained at 50° C. or lower, 627.0 g (4.4 moles) of H6XDA was introduced for 1 hour. Upon completion of the introduction, the internal temperature of Reactor 1 was lowered to 10° C., and it was stirred for 1 hour. The internal temperature of Reactor 2 to which 2,640.0 g of diethyl ether had been charged was lowered to −5° C. The mixture in Reactor 1 was slowly added dropwise to Reactor 2 at 0° C. or lower. Upon completion of the addition, the diamine hydrochloride composition containing H6XDA-2HCl was separated by vacuum filtration using a filter, and the filtered diethyl ether was recovered for reuse. Thereafter, the separated diamine hydrochloride composition was dried under vacuum at 90° C. and 0.5 torr to remove the residual solvent and water.

Example A7

A reactor was charged with 1,009.4 g (9.46 moles) of an aqueous solution of 35% hydrochloric acid, followed by lowering the internal temperature of the reactor to 15° C. with stirring. While the temperature of the reactor was maintained at 50° C. or lower, 490.1 g (4.4 moles) of HDA was introduced for 1 hour. Upon completion of the introduction, the internal temperature of the reactor was lowered to 10° C., and it was stirred for 1 hour. Thereafter, 1,320.0 g of tetrahydrofuran was introduced, and the internal temperature of the reactor was lowered to −5° C., followed by stirring for 1 hour. Upon completion of the reaction, the diamine hydrochloride composition containing HDA.2HCl was separated by vacuum filtration using a filter, and the filtered tetrahydrofuran was recovered for reuse. Thereafter, the separated diamine hydrochloride composition was dried under vacuum at 90° C. and 0.5 torr to remove the residual solvent and water.

Example A8

Reactor 1 was charged with 1,009.4 g (9.46 moles) of an aqueous solution of 35% hydrochloric acid, followed by lowering the internal temperature of Reactor 1 to 15° C. with stirring. While the temperature of Reactor 1 was maintained at 50° C. or lower, 812.0 g (4.4 moles) of IPDA was introduced for 1 hour. Upon completion of the introduction, the internal temperature of Reactor 1 was lowered to 10° C., and it was stirred for 1 hour. The internal temperature of Reactor 2 to which 2,640.0 g of diethyl ether had been charged was lowered to −5° C. The mixture in Reactor 1 was slowly added dropwise to Reactor 2 at 0° C. or lower. Upon completion of the addition, the diamine hydrochloride composition containing IPDA.2HCl was separated by vacuum filtration using a filter, and the filtered diethyl ether was recovered for reuse. Thereafter, the separated diamine hydrochloride composition was dried under vacuum at 90° C. and 0.5 torr to remove the residual solvent and water.

The process conditions of Examples A1 to A8 are summarized in Tables 1 and 2 below.

TABLE 1

|  | Ex. A1 | Ex. A2 | Ex. A3 | Ex. A4 | Ex. A5 |
| --- | --- | --- | --- | --- | --- |
| Aqueous hydrochloric acid solution | 963.5 g | 986.5 g | 1,009.4 g | 1,032.3 g | 1,055.3 g |
| Internal temp. of the reactor | 50° C. | 50° C. | 50° C. | 50° C. | 50° C. |
| m-XDA | 600 g | 600 g | 600 g | 600 g | 600 g |
| Organic solvent | Et$_2$O 1,200 g | i-PrOH 1,260 g | THF 1,320 g | i-BuOH 1,440 g | MEK 1,500 g |
| Vacuum condition | 0.1 Torr | 0.1 Torr | 0.1 Torr | 0.08 Torr | 0.05 Torr |
| Yield of a hydrochloride composition | 88% | 88% | 91% | 92% | 92% |

TABLE 1-continued

|  | Ex. A1 | Ex. A2 | Ex. A3 | Ex. A4 | Ex. A5 |
|---|---|---|---|---|---|
| Water content in the hydrochloride composition | 2% | 2% | 3% | 3% | 1% |

TABLE 2

|  | Ex. A6 | Ex. A7 | Ex. A8 |
|---|---|---|---|
| Aqueous hydrochloric acid solution | 1,009.4 g | 1,009.4 g | 1009.4 g |
| Internal temp. of the reactor | 50° C. | 50° C. | 50° C. |
| Diamine | 627 g | 490 g | 812 g |
| Organic solvent | Diethyl ether, 2,640 g | THF 1,320 g | Diethyl ether, 2,640 g |
| Yield of the hydrochloride composition | 70% | 91% | 72% |

Preparation of a diisocyanate composition

Examples 1-1 and 1-2

Reactor A was charged with 800 g of the m-XDA hydrochloride composition prepared in Example A3 and 3,550 g of ODCB, which was heated at about 125° C. with stirring. Reactor B was charged with 950 g of a triphosgene (BTMC) composition containing less than 1% by weight of carbon tetrachloride ($CCl_4$) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. It was cooled to 10° C., and the remaining solids were filtered using celite. Thereafter, the organic solvent (ODCB) was removed, and m-XDI was purified by distillation under the following distillation conditions. The removal of the organic solvent was carried out for 8 hours at a pressure of 0.5 torr or less and a temperature of 60° C. In addition, the distillation of m-XDI was carried out for 10 hours at a pressure of 0.5 torr or less and a temperature of 120° C.

Example 1-3

Reactor A was charged with 823 g of the diamine hydrochloride composition prepared in Example A6 and 3,550 g of ODCB, which was heated at about 125° C. with stirring. Reactor B was charged with 950 g of a triphosgene (BTMC) composition containing less than 1% by weight of carbon tetrachloride ($CCl_4$) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 3 to 4 hours. Upon completion of the reaction, nitrogen gas was blown into the solvent with bubbling at 125° C. to degas. Thereafter, it was cooled to 10° C., and the remaining solids were filtered using celite. The organic solvent (ODCB) was removed, and distillation was carried out to obtain a diisocyanate composition containing H6XDI. Here, the removal of the organic solvent was carried out for 8 hours at a pressure of 0.5 torr or less and a temperature of 60° C. In addition, the distillation was carried out for 10 hours at a temperature of 120° C. and a pressure of 0.5 torr or less.

Example 1-4

Reactor A was charged with 723 g of the diamine hydrochloride composition prepared in Example A7 and 3,550 g of ODCB, which was heated at about 125° C. with stirring. Reactor B was charged with 950 g of a triphosgene (BTMC) composition containing less than 1% by weight of carbon tetrachloride ($CCl_4$) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 3 to 4 hours. Upon completion of the reaction, nitrogen gas was blown into the solvent with bubbling at 125° C. to degas. Thereafter, it was cooled to 10° C., and the remaining solids were filtered using celite to obtain a diisocyanate composition containing HDI. Thereafter, the organic solvent in the diisocyanate composition was removed, and distillation was carried out. Here, the removal of the organic solvent was carried out for 8 hours at a pressure of 0.5 torr or less and a temperature of 60° C. In addition, the distillation was carried out for 10 hours at a temperature of 120° C. and a pressure of 0.5 torr or less.

Example 1-5

Reactor A was charged with 984 g of the diamine hydrochloride composition prepared in Example A8 and 3,550 g of ODCB, which was heated at about 125° C. with stirring. Reactor B was charged with 950 g of a triphosgene (BTMC) composition containing less than 1% by weight of carbon tetrachloride ($CCl_4$) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 3 to 4 hours. Upon completion of the reaction, nitrogen gas was blown into the solvent with bubbling at 125° C. to degas. Thereafter, it was cooled to 10° C., and the remaining solids were filtered using celite to obtain a diisocyanate composition containing IPDI. Thereafter, the organic solvent in the diisocyanate composition was removed, and distillation was carried out. Here, the removal of the organic solvent was carried out for 8 hours at a pressure of 0.5 torr or less and a temperature of 60° C. In addition, the distillation was carried out for 10 hours at a temperature of 120° C. and a pressure of 0.5 torr or less.

Comparative Examples 1-1 and 1-2

The procedures of Example 1-1 were repeated, except that a diisocyanate composition was prepared using a triphosgene composition containing 1% by weight or more of carbon tetrachloride.

Comparative Example 1-3

The procedures of Example 1-3 were repeated, except that a diisocyanate composition was prepared using a triphosgene composition containing 1% by weight or more of carbon tetrachloride.

Comparative Example 1-4

The procedures of Example 1-4 were repeated, except that a diisocyanate composition was prepared using a triphosgene composition containing 1% by weight or more of carbon tetrachloride.

Comparative Example 1-5

The procedures of Example 1-5 were repeated, except that a diisocyanate composition was prepared using a triphosgene composition containing 1% by weight or more of carbon tetrachloride.

<Preparation of an Optical Lens>

As shown in Table 3 below, the diisocyanate composition (main component: m-XDI, H6XDI, HDI, or IPDI) prepared in the Examples or the Comparative Examples, 5,7-dimercaptomethyl-1,11-dimercapto-3,6-trithiaundecane (BET) as a polythiol, and a tin-based catalyst as an additive were uniformly mixed and defoamed at 600 Pa for 1 hour to prepare a polymerizable composition.

The polymerizable composition was filtered through a Teflon filter of 3 μm and injected into a glass mold assembled with an adhesive tape. The polymerizable composition injected into the mold was subjected to a first polymerized at a temperature of 10 to 35° C. for 3 to 9 hours, a second polymerization at a temperature of 35 to 60° C. for 3 to 9 hours, and a third polymerization at a temperature exceeding 60° C. for 2 to 7 hours. Upon completion of the polymerization, the plastic molded article (optical lens) was released from the mold and subjected to further curing at 130° C. for 2 hours.

TABLE 3

| | Polymerizable composition | | | |
|---|---|---|---|---|
| | Diisocyanate composition | | | |
| Type | Part by weight | Main component | Polythiol (BET) Part by weight | Additive Catalyst |
| Ex. 1-1 | 50.7 | m-XDI | 49.3 | 0.01 |
| Ex. 1-2 | 50.7 | m-XDI | 49.3 | 0.01 |
| Ex. 1-3 | 48.6 | H6XDI | 51.4 | 0.05 |
| Ex. 1-4 | 48.6 | HDI | 51.4 | 0.05 |
| Ex. 1-5 | 48.2 | IPDI | 54.8 | 0.05 |
| C. Ex. 1-1 | 50.7 | m-XDI | 49.3 | 0.01 |
| C. Ex. 1-2 | 50.7 | m-XDI | 49.3 | 0.01 |
| C. Ex. 1-3 | 48.6 | H6XDI | 51.4 | 0.05 |
| C. Ex. 1-4 | 48.6 | HDI | 51.4 | 0.05 |
| C. Ex. 1-5 | 48.2 | IPDI | 54.8 | 0.05 |

<Evaluation Method>

The Examples and the Comparative Examples were evaluated as follows.

(1) Refractive Index (Nd20)

The solid-phase refractive index (nd20) was measured at 20° C. using an Abbe refractometer DR-M4.

(2) Yellow Index (Y.I.) and Light Transmittance

An optical lens was prepared in the form of a cylinder with a radius of 16 mm and a height of 45 mm. Light was transmitted in the height direction to measure the yellow index and transmittance. The yellow index was calculated by the following equation based on the values of x and y, which are the measurement results. Y.I.=(234x+106y)/y.

(3) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(4) Measurement of ICP-MS

Analysis instrument: ICP-OES (Inductively Coupled Plasma-Optical Emission Spectrometer)
Instrument detail: 730ES of Agilent
Light source: Axially viewed Plasma system
Detector: 167-785 nm wavelength CCD (charge coupled device) detector
Pretreatment of a specimen: directly measured without pretreatment (5) APHA A standard solution was prepared in 5 units of APHA in compliance with JIS K 0071-1 standard. The APHA value of the composition was compared with the prepared standard solution with the naked eyes, and the APHA value of the most similar color was taken.

(6) Haze

The optical lens was irradiated to a projector in a darkroom to observe whether the optical lens was cloudy or had any opaque material with the naked eyes.

TABLE 4

| | BTMC composition | Optical lens | | | | | |
|---|---|---|---|---|---|---|---|
| | | Diisocyanate composition | | | | | Refractive |
| | Content of CCl$_4$ | APHA | Haze | Stria | Transmittance | Y.I. | index |
| Ex. 1-1 | 0.2% by weight | 5 | Absent | Absent | 90% | 18 | 1.669 |
| Ex. 1-2 | 0.8% by weight | 5 | Absent | Absent | 90% | 19 | 1.669 |
| Ex. 1-3 | 0.2% by weight | 5 | Absent | Absent | 91% | 18 | 1.623 |
| Ex. 1-4 | 0.2% by weight | 5 | Absent | Absent | 89% | 19 | 1.624 |
| Ex. 1-5 | 0.2% by weight | 5 | Absent | Absent | 90% | 18 | 1.596 |
| C. Ex. 1-1 | 1.5% by weight | 15 | Present | Present | 77% | 25 | 1.668 |
| C. Ex. 1-2 | 2.1% by weight | 20 | Present | Present | 75% | 27 | 1.668 |
| C. Ex. 1-3 | 1.5% by weight | 15 | Present | Present | 75% | 25 | 1.668 |
| C. Ex. 1-4 | 1.5% by weight | 15 | Present | Present | 78% | 26 | 1.668 |
| C. Ex. 1-5 | 1.5% by weight | 15 | Present | Present | 78% | 26 | 1.668 |

As shown in the above table, the optical lenses prepared using a diamine hydrochloride and a triphosgene composition according to the Examples were excellent in refractive index and transmittance. Thus, they are suitable for use as an optical lens of high quality.

In particular, in Examples 1-1 to 1-5 in which a triphosgene composition containing less than 1% by weight of carbon tetrachloride was used to prepare a diisocyanate composition, the color and haze were excellent, and the optical lenses had no stria with high transmittance and low yellow index.

In contrast, in Comparative Examples 1-1 to 1-5 in which a triphosgene composition containing 1% by weight or more of carbon tetrachloride was used to prepare a diisocyanate composition, the color and haze were poor, and the optical lenses had striae with low transmittance and high yellow index.

Preparation of a Diamine Hydrochloride Composition

Examples A1 to A5

Tests were conducted in the same manner as in Examples A1 to A5.

Comparative Example A1

The same reactor as in Example A1 was charged with 846 g of orthodichlorobenzene (ODCB) as a reaction solvent. 136.2 g (1.0 mole) of m-XDI and 621 g of ODCB were charged to the raw material tank (in a total amine concentration of 8.5% by weight). Next, the internal temperature of the reactor was raised to 120° C. under atmospheric pressure. Thereafter, hydrogen chloride gas began to be introduced through the hydrogen chloride gas injection line. At the same time, the entire amount of the amine diluted with the solvent was introduced from the raw material tank by a raw material charging pump over 2 hours. Upon completion of the reaction, the obtained hydrochloride slurry (yield 90%) had low fluidity, and a large amount of the hydrochloride composition was left in the reactor in the process of separating the hydrochloride composition.

Comparative Example A2

The same procedures as in Example A1 were repeated, except that a diamine hydrochloride composition was prepared without using an organic solvent (yield 49%).

Preparation of a Diisocyanate Composition

Examples 2-1 to 2-3

Step (1): Preparation of a Triphosgene (BTMC) Composition

A commercially purchased triphosgene composition was dissolved in orthodichlorobenzene (ODCB) in 8% by weight. The b* value according to the CIE color coordinate was measured. If it was 1.2 or less, the composition was used in the next step without separate treatment. If it exceeded 1.2, the composition was washed with a 10 to 30% sodium chloride solution at 0° C. and then dried for 8 hours at 60° C. and 0.5 Torr or less, whereby the b* value was adjusted to 1.2 or less (see Table 6 below).

Step (2): Preparation of a m-XDI Composition

Reactor A was charged with 800 g of the m-XDA hydrochloride composition prepared in Example A3 and 3,550 g of ODCB, which was heated at about 125° C. with stirring. Reactor B was charged with 950 g of a triphosgene (BTMC) composition obtained in Step (1) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. Thereafter, it was cooled to 10° C., and the remaining solids were filtered using celite. The filtered solvent and the produced m-XDI were purified by distillation under the following distillation conditions. The removal of the organic solvent (ODCB) was carried out for 8 hours at a pressure of 0.5 torr or less and a temperature of 60° C. The distillation of m-XDI was carried out for 10 hours at a pressure of 0.1 torr or less and a temperature of 120° C. As a result, a m-XDI composition was obtained.

Comparative Examples 2-1 and 2-2

The procedures of Example 2-1 were repeated, except that a m-XDI composition was prepared using a commercially purchased triphosgene composition without separate treatment. In such event, the b* value according to the CIE color coordinate was 1.2 or more when the triphosgene composition was dissolved in orthodichlorobenzene at a concentration of 8% by weight.

TABLE 5

| | Ex. A1 | Ex. A2 | Ex. A3 | Ex. A4 | Ex. A5 | C. Ex. A1 | C. Ex. A2 |
|---|---|---|---|---|---|---|---|
| Aqueous hydrochloric acid solution | 963.5 g | 986.5 g | 1,009.4 g | 1,032.3 g | 1,055.3 g | HCl gas | 963.5 g |
| Internal temp. of the reactor | 50° C. | 50° C. | 50° C. | 50° C. | 50° C. | 120° C. | 50° C. |
| m-XDA | 600 g | 600 g | 600 g | 600 g | 600 g | 136.2 g | 600 g |
| Organic solvent | $Et_2O$ 1,200 g | i-PrOH 1,260 g | THF 1,320 g | i-BuOH 1,440 g | MEK 1,500 g | ODCB 846 g + 621 g | — |
| Vacuum condition | 0.1 Torr | 0.1 Torr | 0.1 Torr | 0.08 Torr | 0.05 Torr | — | 0.1 Torr |
| Yield of the hydrochloride composition | 88% | 88% | 91% | 92% | 92% | 90% | 49% |
| Water content in the hydrochloride composition | 2% | 2% | 3% | 3% | 1% | — | — |

<Preparation of an Optical Lens>

49.3 parts by weight of 4,8-bis(mercaptomethyl)-3,6,9-trithiaundecane-1,11-dithiol, 50.7 parts by weight of the m-XDI composition prepared in the Examples or the Comparative Examples, 0.01 part by weight of dibutyltin dichloride, and 0.1 part by weight of a phosphate ester release agent (ZELEC™ UN Stepan) were homogeneously mixed, which was defoamed at 600 Pa for 1 hour, filtered through a Teflon filter of 3 µm, and injected into a mold made of a glass mold and a tape. The mold was maintained at 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens.

<Evaluation Method>

The Examples and the Comparative Examples were evaluated as follows.

(1) Measurement of b*

The b* value was measured using a spectrophotometer (Colormate, Sinko Corporation). A liquid sample was filled in a quartz cell having a thickness of 10 mm, and a solid sample was dissolved in an organic solvent (ODCB) at 8% by weight. The lower the b* value, the better the color.

(2) Refractive Index (Nd20)

The solid-phase refractive index (nd20) was measured at 20° C. using an Abbe refractometer DR-M4.

(3) Yellow Index (Y.I.) and Light Transmittance

An optical lens was prepared in the form of a cylinder with a radius of 16 mm and a height of 45 mm. Light was transmitted in the height direction to measure the yellow index and transmittance. The yellow index was calculated by the following equation based on the values of x and y, which are the measurement results. Y.I.=(234x+106y)/y.

(4) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(5) ICP-MS Measurement

Analysis instrument: ICP-OES (Inductively Coupled Plasma-Optical Emission Spectrometer)
Instrument detail: 730ES of Agilent
Light source: Axially viewed Plasma system
Detector: 167-785 nm wavelength CCD (charge coupled device) detector
Pretreatment of a specimen: directly measured without pretreatment (6) APHA A standard solution was prepared in 5 units of APHA in compliance with JIS K 0071-1 standard. The APHA value of the composition was compared with the prepared standard solution with the naked eyes, and the APHA value of the most similar color was taken.

(7) Haze

The optical lens was irradiated to a projector in a darkroom to observe whether the optical lens was cloudy or had any opaque material with the naked eyes.

TABLE 6

| | BTMC composition | | | m-XDI composition | | Optical lens | | | |
|---|---|---|---|---|---|---|---|---|---|
| | Initial b* | BTMC washing | Before introduction b* | APHA | Haze | Stria | Transmittance | Y.I. | Refractive index |
| Ex. 2-1 | 0.5 | x | 0.5 | 5 | Absent | Absent | 90% | 18 | 1.669 |
| Ex. 2-2 | 1.5 | o | 0.5 | 5 | Absent | Absent | 90% | 18 | 1.669 |
| Ex. 2-3 | 2.0 | o | 0.7 | 5 | Absent | Absent | 88% | 19 | 1.669 |
| C. Ex. 2-1 | 1.5 | x | 1.5 | 15 | Absent | Absent | 88% | 32 | 1.668 |
| C. Ex. 2-2 | 2.0 | x | 2.0 | 20 | Absent | Absent | 85% | 36 | 1.668 |

As shown in the above table, the optical lenses prepared using a diamine hydrochloride and a triphosgene composition according to the Examples were excellent in refractive index and transmittance. Thus, they are suitable for use as an optical lens of high quality.

In particular, in Examples 2-1 to 2-3 in which a triphosgene composition having a b* value of less than 1.2 was used to prepare a diisocyanate composition, the color and haze were excellent, and the optical lenses had no stria with high transmittance and low yellow index.

In contrast, in Comparative Examples 2-1 and 2-2 in which a triphosgene composition having a b* value of 1.2 or more was used to prepare a diisocyanate composition, the color and haze were poor, and the optical lenses had low transmittance and high yellow index.

Preparation Example: Adjustment of the Content of Water in BTMC

The content of water in triphosgene (BTMC) to be used in the reaction was measured. If it was 200 ppm or less, the triphosgene was used in the reaction as it was. If it exceeded 200 ppm, the water content was adjusted by washing and/or drying it under the conditions shown in Table 7 below.

The procedures for measuring the water content were as follows. First, the Karl Fischer reagent for the measurement of moisture was filled in a vaporized moisture meter (KEM, MKS-710S) installed in a glove box filled with dried nitrogen. The flow rate of nitrogen gas was 200 ml/minute, and the internal sublimation temperature was set to 120° C. Preliminary titration was performed to stabilize it until the draft value became 0.10 µg/s or less. Then, the moisture content was measured (back purge 30 minutes, cell purge 30 minutes, measurement time 40 minutes).

TABLE 7

| | Content of water in BTMC (ppm) | | Washing Solvent | drying | |
|---|---|---|---|---|---|
| | Initial | Final | | Temp. (° C.) | Time (hr) |
| Prep. Ex. A | 20 | 20 | — | — | — |
| Prep. Ex. B | 311 | 25 | THF | 60 | 4 |
| Prep. Ex. C | 311 | 15 | — | 60 | 8 |
| Prep. Ex. D | 311 | 56 | THF | 20 | 8 |
| Prep. Ex. E | 311 | 45 | Acetone | 50 | 4 |
| Prep. Ex. F | 311 | 311 | — | — | — |
| Prep. Ex. G | 311 | 256 | — | 5 | 8 |
| Prep. Ex. H | 311 | 29 | THF | 100 | 4 |
| Prep. Ex. I | 311 | 222 | Cyclohexanone | 60 | 8 |
| Prep. Ex. J | 311 | 240 | Pyridine | 60 | 8 |

Examples 3-1 to 3-5: Preparation of a Diisocyanate Composition

Step (1): Preparation of a Diamine Hydrochloride Composition

A reactor was charged with 1,009.4 g (9.46 moles) of an aqueous solution of 35% hydrochloric acid, followed by lowering the internal temperature of the reactor to 15° C. with stirring. While the temperature of the reactor was maintained at 60° C., 600.0 g (4.4 moles) of m-XDA was introduced for 1 hour. Upon completion of the introduction, the internal temperature of the reactor was lowered to 10° C., and it was stirred for 1 hour. Thereafter, 1,500.0 g of tetrahydrofuran (THF) was introduced, and the internal temperature of the reactor was lowered to −5° C., followed by stirring for 1 hour. Upon completion of the reaction, the diamine hydrochloride composition containing m-XDA.2HCl was separated by vacuum filtration using a filter, and the filtered tetrahydrofuran was recovered for reuse. In order to remove the residual solvent and water, the separated diamine hydrochloride composition was vacuum dried at 90° C. and 0.5 torr.

Step (2): Preparation of a Diisocyanate Composition

Reactor A was charged with 800 g of the diamine hydrochloride composition prepared above and 3,550 g of ODCB, which were heated at about 125° C. with stirring. Reactor B was charged with 950 g of triphosgene (BTMC of Preparation Examples A to E) whose water content had been adjusted and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. Thereafter, it was cooled to 10° C., and the remaining solids were filtered using celite. The organic solvent (ODCB) was removed, and distillation was carried out to obtain a diisocyanate composition containing m-XDI. Here, the removal of the organic solvent was carried out for 8 hours at a pressure of 0.5 torr or less and a temperature of 60° C. The distillation was carried out for 10 hours at a pressure of 0.5 torr or less and a temperature of 120° C.

Comparative Examples 3-1 to 3-5: Preparation of a Diisocyanate Composition

The same procedures as in the above examples were repeated, except that, as the triphosgene used in step (2), the triphosgene (BTMC of Preparation Example F) whose water content had not been adjusted or the triphosgene (Preparation Examples G to J), which had not been properly washed or dried to control the water content, was used to prepare a diisocyanate composition.

Example 3-6

Step (1): Preparation of a Diamine Hydrochloride Composition

Reactor 1 was charged with 1,009.4 g (9.46 moles) of an aqueous solution of 35% hydrochloric acid, followed by lowering the internal temperature of Reactor 1 to 15° C. with stirring. While the temperature of Reactor 1 was maintained at 50° C. or lower, 627.0 g (4.4 moles) of H6XDA was introduced for 1 hour. Upon completion of the introduction, the internal temperature of Reactor 1 was lowered to 10° C., and it was stirred for 1 hour. The internal temperature of Reactor 2 to which 2,640.0 g of diethyl ether had been charged was lowered to −5° C. The mixture in Reactor 1 was slowly added dropwise to Reactor 2 at 0° C. or lower. Upon completion of the addition, the diamine hydrochloride composition containing H6XDA-2HCl was separated by vacuum filtration using a filter, and the filtered diethyl ether was recovered for reuse. Thereafter, the separated diamine hydrochloride composition was dried under vacuum at 90° C. and 0.5 torr to remove the residual solvent and water.

Step (2): Preparation of a Diisocyanate Composition

Reactor A was charged with 823 g of the diamine hydrochloride composition prepared above and 3,550 g of ODCB, which was heated at about 125° C. with stirring. Reactor B was charged with 950 g of triphosgene (BTMC of Preparation Example A) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 3 to 4 hours. Upon completion of the reaction, nitrogen gas was blown into the solvent with bubbling at 125° C. to degas. Thereafter, it was cooled to 10° C., and the remaining solids were filtered using celite. The organic solvent (ODCB) was removed, and distillation was carried out to obtain a diisocyanate composition containing H6XDI. Here, the removal of the organic solvent was carried out for 8 hours at a pressure of 0.5 torr or less and a temperature of 60° C. In addition, the distillation was carried out for 10 hours at a temperature of 120° C. and a pressure of 0.5 torr or less.

Example 3-7

Step (1): Preparation of a Diamine Hydrochloride Composition

A reactor was charged with 1,009.4 g (9.46 moles) of an aqueous solution of 35% hydrochloric acid, followed by lowering the internal temperature of the reactor to 15° C. with stirring. While the temperature of the reactor was maintained at 50° C. or lower, 490.1 g (4.4 moles) of HDA was introduced for 1 hour. Upon completion of the introduction, the internal temperature of the reactor was lowered to 10° C., and it was stirred for 1 hour. Thereafter, 1,320.0 g of tetrahydrofuran was introduced, and the internal temperature of the reactor was lowered to −5° C., followed by stirring for 1 hour. Upon completion of the reaction, the diamine hydrochloride composition containing HDA.2HCl was separated by vacuum filtration using a filter, and the filtered tetrahydrofuran was recovered for reuse. Thereafter, the separated diamine hydrochloride composition was dried under vacuum at 90° C. and 0.5 torr to remove the residual solvent and water.

Step (2): Preparation of a Diisocyanate Composition

Reactor A was charged with 723 g of the diamine hydrochloride composition prepared above and 3,550 g of ODCB, which was heated at about 125° C. with stirring. Reactor B was charged with 950 g of triphosgene (BTMC of Preparation Example A) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 3 to 4 hours. Upon completion of the reaction, nitrogen gas was blown into the solvent with bubbling at 125° C. to degas. Thereafter, it was cooled to 10° C., and the remaining solids were filtered using celite to obtain a diisocyanate composition containing HDI. Thereafter, the organic solvent in the diisocyanate composition was removed, and distillation was carried out. Here, the removal of the organic solvent was carried out for 8 hours at a pressure of 0.5 torr or less and a temperature of 60° C. In addition, the distillation was carried out for 10 hours at a temperature of 120° C. and a pressure of 0.5 torr or less.

Example 3-8

Step (1): Preparation of a Diamine Hydrochloride Composition

Reactor 1 was charged with 1,009.4 g (9.46 moles) of an aqueous solution of 35% hydrochloric acid, followed by lowering the internal temperature of Reactor 1 to 15° C. with stirring. While the temperature of Reactor 1 was maintained at 50° C. or lower, 812.0 g (4.4 moles) of IPDA was introduced for 1 hour. Upon completion of the introduction, the internal temperature of Reactor 1 was lowered to 10° C., and it was stirred for 1 hour. The internal temperature of Reactor 2 to which 2,640.0 g of diethyl ether had been charged was lowered to −5° C. The mixture in Reactor 1 was slowly added dropwise to Reactor 2 at 0° C. or lower. Upon completion of the addition, the diamine hydrochloride composition containing IPDA.2HCl was separated by vacuum filtration using a filter, and the filtered diethyl ether was recovered for reuse. Thereafter, the separated diamine hydrochloride composition was dried under vacuum at 90° C. and 0.5 torr to remove the residual solvent and water.

Step (2): Preparation of a Diisocyanate Composition

Reactor A was charged with 984 g of the diamine hydrochloride composition prepared above and 3,550 g of ODCB, which was heated at about 125° C. with stirring. Reactor B was charged with 950 g of triphosgene (BTMC of Preparation Example A) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 3 to 4 hours. Upon completion of the reaction, nitrogen gas was blown into the solvent with bubbling at 125° C. to degas. Thereafter, it was cooled to 10° C., and the remaining solids were filtered using celite to obtain a diisocyanate composition containing IPDI. Thereafter, the organic solvent in the diisocyanate composition was removed, and distillation was carried out. Here, the removal of the organic solvent was carried out for 8 hours at a pressure of 0.5 torr or less and a temperature of 60° C. In addition, the distillation was carried out for 10 hours at a temperature of 120° C. and a pressure of 0.5 torr or less.

Comparative Example 3-6

The same procedures as in Example 3-6 were repeated, except that, as the triphosgene used in step (2), the triphosgene (BTMC of Preparation Example F) whose water content had not been adjusted was used to prepare a diisocyanate composition.

Comparative Example 3-7

The same procedures as in Example 3-7 were repeated, except that, as the triphosgene used in step (2), the triphosgene (BTMC of Preparation Example F) whose water content had not been adjusted was used to prepare a diisocyanate composition.

Comparative Example 3-8

The same procedures as in Example 3-8 were repeated, except that, as the triphosgene used in step (2), the triphosgene (BTMC of Preparation Example F) whose water content had not been adjusted was used to prepare a diisocyanate composition.

<Preparation of an Optical Lens>

As shown in Table 8 below, the diisocyanate composition (main component: m-XDI, H6XDI, HDI, or IPDI) prepared in the Examples or the Comparative Examples, 5,7-dimercaptomethyl-1,11-dimercapto-3,6-trithiaundecane (BET) as a polythiol, and a tin-based catalyst as an additive were uniformly mixed and defoamed at 600 Pa for 1 hour to prepare a polymerizable composition.

The polymerizable composition was filtered through a Teflon filter of 3 μm and injected into a glass mold assembled with an adhesive tape. The polymerizable composition injected into the mold was subjected to a first polymerized at a temperature of 10° C. to 35° C. for 3 hours to 9 hours, a second polymerization at a temperature of 35° C. to 60° C. for 3 hours to 9 hours, and a third polymerization at a temperature exceeding 60° C. for 2 to 7 hours. Upon completion of the polymerization, the plastic molded article (optical lens) was released from the mold and subjected to further curing at 130° C. for 2 hours.

BET:

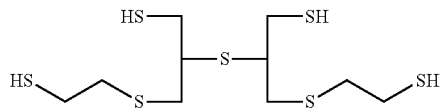 [SMILES: SCCSCC(CS)SC(CS)CSCCS]

5,7-dimercaptomethyl-1,11-dimercapto-3,6-trithiaundecane m-XDI:

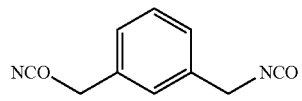

m-xylylene diisocyanate
H6XDI:

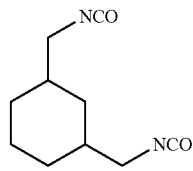

hydrogenated xylylene diisocyanate
HDI:

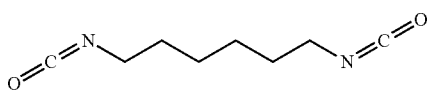 [SMILES: O=C=NCCCCCCN=C=O]

hexamethylene diisocyanate
IPDI:

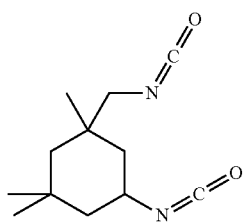 [SMILES: CC1(C)CC(N=C=O)CC(C)(CN=C=O)C1]

isophorone diisocyanate

TABLE 8

| | Polymerizable composition | | | |
|---|---|---|---|---|
| | Diisocyanate composition | | | |
| Type | Part by weight | Main component | Polythiol (BET) Part by weight | Additive Catalyst |
| Ex. 3-1 | 50.7 | m-XDI | 49.3 | 0.01 |
| Ex. 3-2 | 50.7 | m-XDI | 49.3 | 0.01 |
| Ex. 3-3 | 50.7 | m-XDI | 49.3 | 0.01 |
| Ex. 3-4 | 50.7 | m-XDI | 49.3 | 0.01 |
| Ex. 3-5 | 50.7 | m-XDI | 49.3 | 0.01 |
| Ex. 3-6 | 48.6 | H6XDI | 51.4 | 0.05 |
| Ex. 3-7 | 48.6 | HDI | 51.4 | 0.05 |
| Ex. 3-8 | 48.2 | IPDI | 54.8 | 0.05 |
| C. Ex. 3-1 | 50.7 | m-XDI | 49.3 | 0.01 |
| C. Ex. 3-2 | 50.7 | m-XDI | 49.3 | 0.01 |
| C. Ex. 3-3 | 50.7 | m-XDI | 49.3 | 0.01 |
| C. Ex. 3-4 | 50.7 | m-XDI | 49.3 | 0.01 |
| C. Ex. 3-5 | 50.7 | m-XDI | 49.3 | 0.01 |
| C. Ex. 3-6 | 48.6 | H6XDI | 51.4 | 0.05 |
| C. Ex. 3-7 | 48.6 | HDI | 51.4 | 0.05 |
| C. Ex. 3-8 | 48.2 | IPDI | 54.8 | 0.05 |

Evaluation Method

The diisocyanate compositions and optical lenses prepared in the Examples and the Comparative Examples were evaluated as follows.

(1) Content of a Diisocyanate

The content of a diisocyanate in the diisocyanate composition was determined by gas chromatography (GC) (instrument: 6890/7890 of Agilent, carrier gas: He, injection temperature 250° C., oven temperature 40° C. to 320° C., column: HP-1, Wax, 30 m, detector: FID, 300° C.)

(2) Distillation Yield

The distillation yield was calculated by measuring the amount of the diisocyanate composition upon the distillation relative to the theoretical amount of the diisocyanate composition produced from the amounts of the diamine hydrochloride composition introduced to the reaction with triphosgene.

(3) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(4) Yellow Index (Y.I.)

An optical lens was prepared in the form of a cylinder with a radius of 16 mm and a height of 45 mm. Light was transmitted in the height direction to measure the yellow index. The yellow index was calculated by the following equation based on the values of x and y, which are the measurement results. Y.I.=(234x+106y)/y.

(5) Cloudiness (Haze)

The optical lens was irradiated to a projector in a darkroom to observe whether the optical lens was cloudy or had any opaque material with the naked eyes.

TABLE 9

| | | Distillation yield (%) | Content of a diisocyanate in the diisocyanate composition (% by weight) | | Optical lens | | |
|---|---|---|---|---|---|---|---|
| | BTMC | | Before distillation | After distillation | Stria | Cloudiness | Y.I. |
| Ex. 3-1 | Prep. Ex. A | 89 | 99.4 | 99.9 | Absent | Absent | 19 |
| Ex. 3-2 | Prep. Ex. B | 88 | 99.3 | 99.9 | Absent | Absent | 20 |
| Ex. 3-3 | Prep. Ex. C | 89 | 99.2 | 99.9 | Absent | Absent | 19 |
| Ex. 3-4 | Prep. Ex. D | 87 | 99.3 | 99.9 | Absent | Absent | 20 |
| Ex. 3-5 | Prep. Ex. E | 89 | 99.3 | 99.9 | Absent | Absent | 20 |
| Ex. 3-6 | Prep. Ex. A | 88 | 99.2 | 99.8 | Absent | Absent | 19 |
| Ex. 3-7 | Prep. Ex. A | 89 | 99.1 | 99.8 | Absent | Absent | 20 |
| Ex. 3-8 | Prep. Ex. A | 89 | 99.0 | 99.8 | Absent | Absent | 19 |
| C. Ex. 3-1 | Prep. Ex. F | 75 | 98.3 | 99.2 | Absent | Slight haze | 22 |

TABLE 9-continued

| | BTMC | Distillation yield (%) | Content of a diisocyanate in the diisocyanate composition (% by weight) | | Optical lens | | |
| --- | --- | --- | --- | --- | --- | --- | --- |
| | | | Before distillation | After distillation | Stria | Cloudiness | Y.I. |
| C. Ex. 3-2 | Prep. Ex. G | 84 | 98.5 | 99.5 | Absent | Slight haze | 23 |
| C. Ex. 3-3 | Prep. Ex. H | 86 | 98.1 | 99.5 | Absent | Slight haze | 22 |
| C. Ex. 3-4 | Prep. Ex. I | 84 | 98.3 | 99.6 | Absent | Slight haze | 21 |
| C. Ex. 3-5 | Prep. Ex. J | | Reaction failing to be carried out | | | | |
| C. Ex. 3-6 | Prep. Ex. F | 78 | 98.1 | 99.3 | Absent | Slight haze | 23 |
| C. Ex. 3-7 | Prep. Ex. F | 77 | 98.2 | 99.2 | Absent | Slight haze | 22 |
| C. Ex. 3-8 | Prep. Ex. F | 79 | 98.4 | 99.1 | Absent | Slight haze | 24 |

As can be seen from the above table, in Examples 3-1 to 3-8 in which triphosgene (Preparation Examples A to E) whose water content had been adjusted was used, the distillation yield and the content of a diisocyanate in the composition were excellent. The optical lenses prepared therefrom were improved in stria, cloudiness, and yellow index.

In contrast, in Comparative Examples 3-1 and 3-6 to 3-8 in which triphosgene (Preparation Example F) whose water content had not been adjusted was used, or in Comparative Examples 3-2 to 3-5 in which triphosgene (Preparation Examples G to J), which had not been properly washed or dried to control the water content, was used, the phosgenation reaction failed to be carried out, or the distillation yield and the content of a diisocyanate in the composition were poor. The optical lenses prepared therefrom had cloudiness and yellowing.

The invention claimed is:

1. A process for preparing a diisocyanate composition, which comprises:
    reacting a diamine hydrochloride composition with a triphosgene composition to obtain a diisocyanate composition,
    wherein the triphosgene composition has a b* value according to the CIE color coordinate of 1.2 or less when dissolved in orthodichlorobenzene at a concentration of 8% by weight, and
    wherein the b* value according to the CIE color coordinate of the triphosgene composition is adjusted by washing the triphosgene composition with a 10% to 30% sodium chloride solution.

2. The process for preparing theft diisocyanate composition of claim 1,
    wherein a decomposition product of triphosgene comprises carbon tetrachloride,
    wherein the content of the carbon tetrachloride is measured and the content of the decomposition product of triphosgene in the triphosgene composition is adjusted to less than 1% by weight by washing the triphosgene composition with diethyl ether at 5° C. or lower.

3. The process for preparing the diisocyanate composition of claim 1, wherein the diamine hydrochloride composition and the triphosgene composition are introduced to the reaction at an equivalent ratio of 1:1 to 5, and the reaction of the diamine hydrochloride composition and the triphosgene composition is carried out at a temperature of 110° C. to 160° C.

4. The process for preparing a diisocyanate composition of claim 1, wherein the diisocyanate composition is obtained by subjecting the reaction resultant obtained by reacting the diamine hydrochloride composition and the triphosgene composition to first distillation at 40° C. to 60° C. for 2 to 8 hours and second distillation at 80° C. to 160° C. for 2 to 10 hours.

5. The process for preparing the diisocyanate composition of claim 1, wherein the diisocyanate composition has an APHA value of 10 or less, the diamine is xylylenediamine, and the diisocyanate composition comprises xylylene diisocyanate.

6. The process for preparing the diisocyanate composition of claim 1, wherein the diamine hydrochloride composition is obtained by reacting a diamine with an aqueous hydrochloric acid solution,
    the aqueous hydrochloric acid solution has a concentration of 20% by weight to 45% by weight, and
    the diamine and the aqueous hydrochloric acid solution are introduced to the reaction at an equivalent ratio of 1:2 to 5 at a temperature of 20° C. to 40° C.

* * * * *